United States Patent
Kwon et al.

(10) Patent No.: US 10,092,548 B2
(45) Date of Patent: Oct. 9, 2018

(54) PHARMACEUTICAL COMPOSITIONS FOR PREVENTING OR TREATING ANGIOGENIC DISEASES COMPRISING INHIBITORS OF NUP153 GENE EXPRESSION OR NUP153 ACTIVITY AS ACTIVE INGREDIENT

(71) Applicant: INDUSTRY-ACADEMIC COOPERATION FOUNDATION, YONSEI UNIVERSITY, Seoul (KR)

(72) Inventors: Ho Jeong Kwon, Seoul (KR); Nam Hee Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 109 days.

(21) Appl. No.: 14/335,895

(22) Filed: Jul. 19, 2014

(65) Prior Publication Data

US 2015/0023973 A1    Jan. 22, 2015

(30) Foreign Application Priority Data

Jul. 19, 2013  (KR) .................. 10-2013-0085670

(51) Int. Cl.
| | | |
|---|---|---|
| *G01N 33/53* | (2006.01) | |
| *A61K 31/4188* | (2006.01) | |
| *G01N 33/50* | (2006.01) | |
| *G01N 33/68* | (2006.01) | |
| *C12N 15/113* | (2010.01) | |

(52) U.S. Cl.
CPC ...... *A61K 31/4188* (2013.01); *C12N 15/1138* (2013.01); *G01N 33/5023* (2013.01); *G01N 33/6875* (2013.01); *C12N 2310/11* (2013.01); *C12N 2310/3233* (2013.01); *G01N 2800/7014* (2013.01)

(58) Field of Classification Search
None
See application file for complete search history.

(56) References Cited

U.S. PATENT DOCUMENTS

2005/0226879 A1   10/2005   Ulmann et al. ............ 424/146.1

OTHER PUBLICATIONS

Salam et al. (2011) Acta Ophthalmologica 89: 405-411.*
Nam Hee Kim et al., R-(-)-b-O-methylsynephrine, a natural product, inhibits VEGF-induced angiogenesis in vitro and in vivo, Biochemical and Biophysical Research Communications 399 (2010) 20-23.
Adamis, A. et al., (1999). "Angiogenesis and ophthalmic disease". *Angiogenesis*. 3:9-14.
Carmeliet, P. et al., (2000). "Angiogenesis in cancer and other diseases". *Nature*. 407:249-257.
Carmeliet, P., (2003). "Angiogenesis in health and disease". *Angiogenesis Focus Nature Medicine*. 9(6):653-660.
Folkman, J. (1972). "Angiogenesis in psoriasis: therapeutic implications". *The Journal of Investigative Dermatology*. 59(1):40-43.
Folkman, J. (1995). "Seminars in medicine of the beth Israel hospital, Boston: clinical application of research on angiogenesis". The New England Journal of Medicine. 333(26):1757-1763.
Zhou, L. et al. (2010). "The nucleoporin Nup153 maintains nuclear envelope architecture and is required for cell migration in tumor cells", *FEBS Letters*, 584:3013-3020.

* cited by examiner

*Primary Examiner* — Michael Pak
(74) *Attorney, Agent, or Firm* — Harness, Dickey & Pierce, P.L.C.

(57) ABSTRACT

The present invention provides a pharmaceutical composition for preventing or treating angiogenic diseases comprising inhibitors of NUP153 gene expression or NUP153 activity as active ingredient and a method for screening an agent for preventing or treating angiogenic diseases. According to the present invention, inhibition of the NUP153 gene expression or the NUP153 activity reduces export of mRNA of a pro-angiogenic factor (VEGF, HGF and bFGF) from nucleus. In addition, inhibition of the NUP153 gene expression or the NUP153 activity has effect that angiogenesis are inhibited by inhibition of invasion and tube formation in a dose-dependent manner without showing toxicity. Therefore, the pharmaceutical composition of the present invention may be used for preventing or treating a variety of angiogenesis-related diseases, and the method for screening of the present invention may be valuably used in finding a new agent for preventing or treating angiogenic diseases.

1 Claim, 16 Drawing Sheets

Specification includes a Sequence Listing.

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 1
ccaccgcaac aagcccagta gttta                                           25

<210> SEQ ID NO 2
<211> LENGTH: 25
<212> TYPE: DNA
<213> ORGANISM: Artificial Sequence
<220> FEATURE:
<223> OTHER INFORMATION: 5-MO

<400> SEQUENCE: 2
ttttccctcc tcctgtcgcc gccat                                           25

<210> SEQ ID NO 3
<211> LENGTH: 25
<212> TYPE: DNA
<213> ORGANISM: Artificial Sequence
<220> FEATURE:
<223> OTHER INFORMATION: sp-MO

<400> SEQUENCE: 3
acattgagac atgttcagac ctgat                                           25

<210> SEQ ID NO 4
<211> LENGTH: 251
<212> TYPE: DNA
<213> ORGANISM: Homo sapiens

<400> SEQUENCE: 4
gaattcttca atccttaaaa ccagtcagct tggagattct ccttttatc ctggaaaaac       60 aacatacggt ggggcagcag ctgctgtaag acagtctaaa ctacgaaata caccttatca    120
ggcaccagtt agaagacaaa tgaaagctaa gcaactcagt gcacaatctt acggtgtgac    180
cagttcaaca gctcggcgaa tattgcagtc tttagagaag atgtcaagcc ctttagcgga    240
tgcaaaagct t                                                         251

<210> SEQ ID NO 5
<211> LENGTH: 251
<212> TYPE: DNA
<213> ORGANISM: Artificial Sequence
<220> FEATURE:
<223> OTHER INFORMATION: Phage Coding Sequence (Translated)

<400> SEQUENCE: 5
gaattcttca atccttaaaa ccagtcagct tggagattct ccttttatc ctggaaaaac       60 aacatacggt ggggcagcag ctgctgtaag acagtctaaa ctacgaaata caccttatca    120
ggcaccagtt agaagacaaa tgaaagctaa gcaactcagt gcacaatctt acggtgtgac    180
cagttcaaca gctcggcgaa tattgcagtc tttagagaag atgtcaagcc ctttagcgga    240
tgcaaaagct t                                                         251
```

PHARMACEUTICAL COMPOSITIONS FOR PREVENTING OR TREATING ANGIOGENIC DISEASES COMPRISING INHIBITORS OF NUP153 GENE EXPRESSION OR NUP153 ACTIVITY AS ACTIVE INGREDIENT

CROSS-REFERENCE TO RELATED APPLICATION

This application claims priority to and the benefit of Korean Patent Application No. 10-2013-0085670, filed on Jul. 19, 2013, the disclosure of which is incorporated herein by reference in its entirety.

BACKGROUND

Field of the Invention

The present invention relates to a pharmaceutical composition for preventing or treating angiogenic diseases including inhibitors of NUP153 gene expression or NUP153 activity as active ingredient and a method for screening an agent for preventing or treating angiogenic diseases.

Background of Technique

Identifying the target protein of a bioactive small molecule is a key step in addressing the mechanism of the compound. Additionally, structural and biological information of a small molecule and its target protein have been applied to the manipulation of biological systems and drug development (Cong et al., 2012; Lindsay, 2003). Indeed, several new functional annotations for disease-related proteins have been successfully defined using bioactive small molecules (Lomenick et al., 2011; Piggott and Karuso, 2008; Sato et al., 2011). For instance, the affinity-based, direct target protein identification of the immunosuppressive agent FK506 (Tacrolimus) characterized FK506 binding protein (FKBP) as an adaptor protein of FK506. The FK506/FKBP complex inhibits the dephosphorylation of nuclear factor of activated T-cells (NFAT) by calcineurin, preventing T-cell activation (Harding et al., 1989; Liu et al., 1991; Siekierka et al., 1989). Owing to this breakthrough, FK506 has been used as a useful chemical genetic probe in calcineurin-mediated signaling and as an immunosuppressive drug in various medical treatments (Furuichi et al., 2003; Jusko et al., 1995). Recent discovery of an antagonist for cytoplasmic dynein from synthetic small molecules using the core structure of the naturally occurring product purealin would be another example of this line of effort (Firestone et al., 2012).

Several cellular target proteins for angiogenesis and their specific inhibitors have been identified. However, recent clinical studies have revealed that inhibition of these target proteins is not sufficient to block the complex biological processes involved in angiogenesis and tumor development. This drawback mainly arises from the diverse genetic heterogeneity in cancer and alternative pathways that lead to drug resistance (Giles et al., 2003; Markman, 2008). Therefore, mining of new therapeutic targets for angiogenesis regulation is crucial to reduce the clinical failure rate of these small molecules and develop better anti-angiogenic therapeutics. Indeed, small molecules with distinct chemical structures identified by phenotype-based angiogenesis screening have provided new target proteins with unknown functions that will eventually provide more options for controlling angiogenesis and its related disorders (Jung et al., 2010; Lin et al., 2008).

R-(−)-β-O-Methylsynephrine (OMe-Syn), a natural small molecule isolated from plants of the Rutaceae family, was reported to inhibit vascular endothelial growth factor (VEGF)-induced angiogenesis in vitro and in vivo (Kim et al., 2010). The simple and unique chemical structure, biological activity, and good membrane permeability strongly implicate OMe-Syn as a useful seed for chemical genetic probe and drug discovery. However, the underlying mechanism regarding on how OMe-Syn suppresses angiogenesis remains to be elucidated. Accordingly, the present inventors have identified the cellular binding protein that is relevant to the anti-angiogenic activity of OMe-Syn. Using a biotinylated affinity probe of OMe-Syn and a T7 phage display of human cDNA-expressed proteome library, the present inventors identified nucleoporin 153 kDa (NUP153) as one of the binding proteins of the compound.

NUP153 is a component of the nuclear pore complex (NPC), which regulates macromolecular transport between the cytoplasm and nucleus as a gated channel (Ahn, 2009; Vasu and Forbes, 2001). Misregulation of this gated channel, including modification of the cargo, changes in nuclear transport machinery, and reformation of NPC itself, might influence cellular function and subsequently lead to tumorigenesis (Kau et al., 2004). Among several nucleoporins (NUPs), NUP153 has been highlighted as a key player in this unique protein complex. NUP153 plays an important role in the export of RNAs and proteins from the nucleus to the cytoplasm (Fahrenkrog et al., 2002). In addition, NUP153 is necessary for regulating basic nuclear localization signal (NLS)-mediated nuclear protein import (Walther et al., 2001). A recent report also highlighted the role of NUP153 in cell cycle regulation (Mackay et al., 2009). However, no report has described the role of NUP153 in angiogenesis. Accordingly, the present inventors have validated the binding of OMe-Syn to NUP153 and investigated the possible biological role of NUP153 in angiogenesis.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have made intensive efforts to develop a pharmaceutical composition for preventing or treating angiogenic diseases. The present inventors have made intensive efforts to develop a pharmaceutical composition for preventing or treating angiogenic diseases. As a result, the present inventors have found out that NUP153 is a target protein of OMe-Syn inhibiting VEGF-induced angiogenesis, an expression of pro-angiogenic factors is reduced and angiogenesis is inhibited through the mechanism of inhibiting invasion and tube formation when the NUP153 gene expression are down-regulated.

Accordingly, it is an aspect of this invention to provide a pharmaceutical composition for preventing or treating angiogenic diseases including inhibitors of NUP153 gene expression or NUP153 activity as active ingredient It is another aspect of this invention to provide a method for preventing or treating angiogenic diseases.

It is further aspect of this invention to provide a method for screening an agent for preventing or treating angiogenic diseases.

Other aspects and advantages of the present invention will become apparent from the following detailed description together with the appended claims and drawings.

BRIEF DESCRIPTION OF THE DRAWINGS

FIG. 1A shows light microscopic images of whole embryos are shown at 30 hpf: (a) DMSO-treated, (b) OMe-Syn (2.5 μM)-treated, and (c) OMe-Syn (5 μM)-treated embryos. FIG. 1B shows fluorescent images showing dose-dependent OMe-Syn suppression of ISV formation: (a) DMSO-treated, (b) OMe-Syn (2.5 μM)-treated, and (c) OMe-Syn (5 μM)-treated embryos. The drawings were selected as representative data from three independent experiments. FIG. 1C shows quantitative analysis of complete ISVs and angiogenic sprouts at 30 hpf. *p<0.005 versus control. Each value represents the mean±SE from three independent experiments. FIG. 1D shows effect of OMe-Syn-treated embryos on viability at 30 hpf, showing no difference in the survival rate following OMe-Syn treatment. FIG. 1E shows that the VEGF mRNA level decreases with OMe-Syn treatment as detected by RT-PCR. β-actin was used as an internal control.

FIG. 2A shows the structure of OMe-Syn. FIG. 2B shows the structure of the biotinylated molecular probe of OMe-Syn (biotinyl-OMe-Syn). FIG. 2C shows the effect of OMe-Syn and biotinyl-OMe-Syn on the proliferation of HUVECs. Cells were treated with the compounds (0-50 μM) for 72 hours, and then cell growth was measured using the MTT colorimetric assay. A similar reduction in cell growth was observed in both treatment groups. FIG. 2D shows the result of phage display biopanning. "Wash" indicates non-specific phages bound to biotinyl-OMe-Syn immobilized on a streptavidin-coated well. FIG. 2E shows the OMe-Syn binding domain of NUP153. OMe-Syn interacts with the mRNA binding site in NUP153. The phage sequences were 100% identical to the N-terminus (amino acids 245-326) of human NUP153 (SEQ ID NO:4).

FIG. 3A shows the phage binding assay of OMe-Syn. Among isolated phages, NUP153-expressing phage specifically bound to OMe-Syn and not to biotin. CaM- and ARMET-expressing phages, which were other possible binding phages of OMe-Syn, did not bind to OMe-Syn. FIG. 3B shows the phage competition assay using NUP153-expressing phage. After pre-incubation with OMe-Syn (50, 100 μM) and NUP153-expressing phage for 1 hour, the phage was immobilized in the OMe-Syn well. FIG. 3C shows the SPR analysis of the interaction between OMe-Syn and recombinant NUP153 (10-27 μM). Bovine serum albumin (BSA) was used as a negative control. FIG. 3D shows the pull-down assay of biotinyl-OMe-Syn and NUP153 using HUVEC lysates. After the lysates bound to biotin or biotinyl-OMe-Syn, the binding complex was pulled down using streptavidin-agarose beads. The supernatant (sup) and bead fractions were detected by western blotting using an antibody against NUP153.

FIG. 4A shows the structure of OMe-Syn, FIG. 4B shows the structure of C1: biphenyl-4-yl 2-(4-guanidinophenyl)acetate, FIG. 4C shows the structure of C2: (2S,3S)—((R)-3-(3,4-dihydroxyphenyl)-1-methoxy-1-oxopropan-2-yl)2-(3,4-dihydroxyphenyl)-4-((E)-3-((R)-3(3,4dihydroxyphenyl)-1-methoxy-1-oxopropan-2-yloxy)-3-oxoprop-1-enyl)-7-hydroxy-2,3-dihydrobenzofuran-3-carboxylate), and FIG. 4D shows the result of SPR analysis. Each compound was immobilized on streptavidin-coated sensor chip and purified NUP153 (20 μM) was used.

FIG. 5A shows the cell proliferation assay. Cells were treated with various concentrations of siNUP153 (0-10) for 24 and 48 hours. FIG. 5B shows mRNA level of NUP153 was confirmed using RT-PCR. GAPDH and β-actin were used as a loading control. FIG. 5C illustrates the Western blots showing the dose-dependent decrease in the expression level of NUP153 by siRNA (0-10 nM). VEGF, bFGF and HGF expression levels were also inhibited by NUP153 depletion. The level of β-tubulin and β-actin was used as an internal control for normalization. FIG. 5D shows NUP153 depletion by siRNA showed a reduction in (a, b) tube formation and (c, d) chemo-invasion of HUVECs in a dose-dependent manner without showing toxicity. Conditioned medium (CM) from HeLa cells was used to treat HUVECs. Arrows indicate broken tubes following knockdown of NUP153. (b) *p<0.025 versus the control; **p<0.001 versus the control. (d) *p<0.002 versus the control; **p<0.001 versus the control. Each value represents the mean±SE from three independent experiments.

In FIG. 6A, the blocking of splicing using MO was confirmed using RT-PCR. FIG. 6B shows the light microscopic images of whole embryos at 30 hpf: (a) control, (b) 5'-MO: translational blocker of NUP153 (8 ng) and (c) sp-MO: splicing blocker of NUP153 (12 ng). FIG. 6C illustrates that NUP153 MO-injected embryos showed a decrease in the number of complete ISVs and angiogenic sprouts without toxicity. The drawings were selected as representative data from three independent experiments. FIG. 6D shows the quantitative analysis of complete ISVs and angiogenic sprouts at 30 hpf. *p<0.005 versus the control. Each value represents the mean±SE from three independent experiments. FIG. 6E shows the effect of NUP153 MO-injected embryos on viability at 30 hpf, showing no toxicity with either MO.

FIG. 7A shows the hematoxylin-stained cross-sections from P17 PBS control (1 μL) (a) and OMe-Syn (20 μM/1 μL PBS) treated (b) mice subjected to OIR, respectively. FIG. 7B shows that, by counting vascular lumens, the inhibitory activity of OMe-Syn was analyzed. Arrows indicate the vascular lumens of new vessels growing into the vitreous. Each value represents the mean (±SD) of three independent experiments (*p<0.05). Scale bars: 50 μm. FIG. 7C illustrates the concept of an embodiment of the present invention. OMe-Syn inhibits angiogenesis by targeting NUP153.

DETAILED DESCRIPTION

Figure 1A:
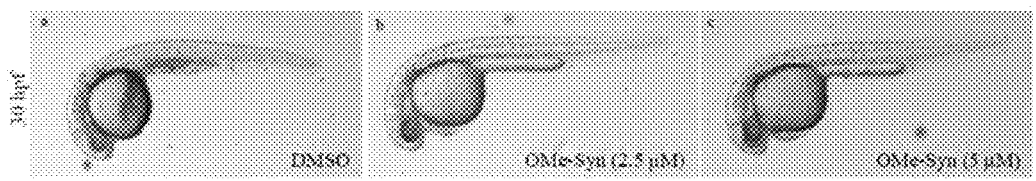
FIGS. 1A through 1E represent effect of OMe-Syn on ISV angiogenesis in fli1a:EGFP transgenic zebrafish embryos.
Figure 1B:
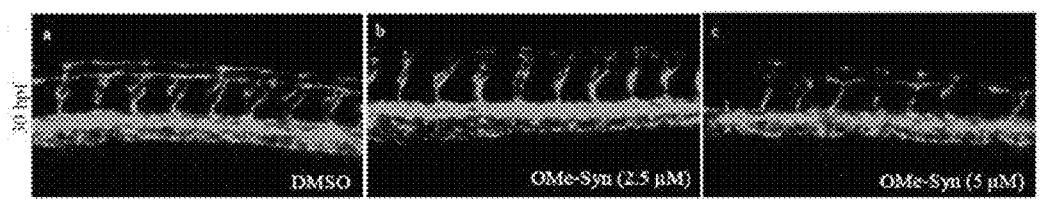
Figure 1C:
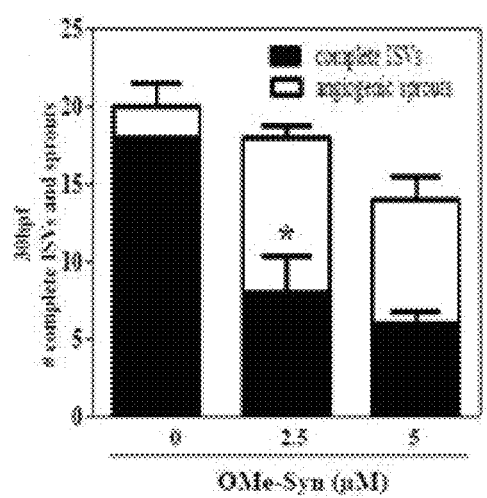
Figure 1D:
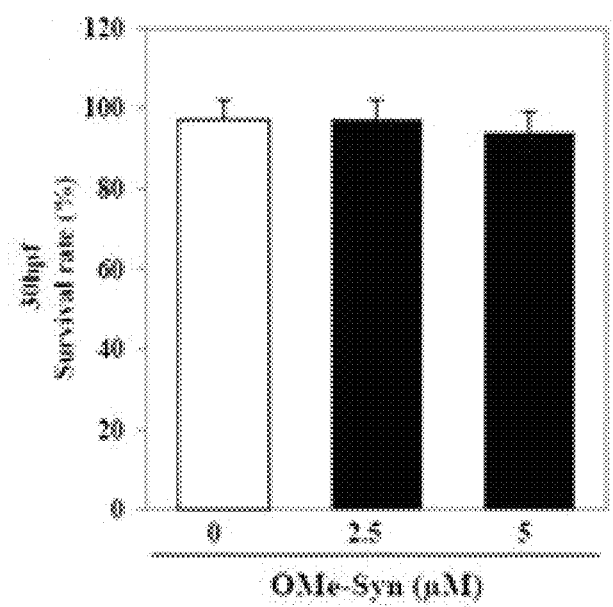

In one aspect of the present invention, there is provided a pharmaceutical composition for preventing or treating angiogenic diseases including inhibitors of NUP153 (nucleoporin 153 kDa) gene expression or NUP153 activity as active ingredient.

The present inventors have made intensive efforts to develop a pharmaceutical composition for preventing or treating angiogenic diseases. The present inventors have made intensive efforts to develop a pharmaceutical composition for preventing or treating angiogenic diseases. As a result, the present inventors have found out that NUP153 is a target protein of OMe-Syn inhibiting VEGF-induced angiogenesis, an expression of pro-angiogenic factors is reduced and angiogenesis is inhibited through the mechanism of inhibiting invasion and tube formation when the NUP153 gene expression are down-regulated.

R-(−)-β-O-Methylsynephrine (OMe-Syn), a natural small molecule isolated from plants of the Rutaceae family, was reported to inhibit vascular endothelial growth factor (VEGF)-induced angiogenesis in vitro and in vivo (Kim et al., 2010). The simple and unique chemical structure, biological activity, and good membrane permeability strongly implicate OMe-Syn as a useful seed for chemical genetic probe and drug discovery. Using a biotinylated affinity probe of OMe-Syn and a T7 phage display of human cDNA-expressed proteome library, the present inventors identified nucleoporin 153 kDa (NUP153) as one of the binding proteins of the compound.

NUP153 of an embodiment of the present invention is a component of the nuclear pore complex (NPC) and has been highlighted as a key player in this unique protein complex. In addition, NUP153 is necessary for regulating basic nuclear localization signal (NLS)-mediated nuclear protein import (Walther et al., 2001).

The inhibitor of NUP153 gene expression or NUP153 activity used as an active ingredient in the pharmaceutical composition of the present, invention includes antisense oligonucleotides, siRNA oligonucleotides, antibodies, aptamers, single chain variable region fragments, peptides, low-molecular-weight compounds, and natural extracts, but is not limited thereto.

According to another embodiment, the inhibitor of NUP153 gene expression is antisense oligonucleotides or siRNA oligonucleotides specifically binding NUP153 gene.

As used herein, the term "antisense oligonucleotide" refers to a DNA, an RNA or a derivative thereof including a nucleotide sequence complementary to a specific mRNA sequence, thus binding to the complementary sequence of the mRNA and inhibiting translation of the mRNA into a protein. The antisense sequence is a DNA or RNA sequence complementary to NUP153 mRNA and capable of binding to the NUP153 mRNA, thus inhibiting translation of the NUP153 mRNA, translocation into the cytoplasm, maturation, or any other activity essential to overall biological functions. The antisense nucleotide may be 6 to 100 bases long, specifically 8 to 60 bases long, more specifically 10 to 40 bases long.

The antisense nucleotide may be modified at one or more base, sugar or backbone positions to improve the desired effect (De Mesmaeker et al., Curr Opin Struct Biol., 5(3): 343-55 (1995)). For example, the nucleotide backbone may be modified with phosphorothioate, phosphotriester, methylphosphonate, single-chain alkyl, cycloalkyl, single-chain heteroatomic, or heterocyclic sugar-sugar bonding. Also, the antisense nucleotide may include one or more substituted sugar moiety. The antisense nucleotide may include a modified base. The modified base may include hypoxanthine, 6-methyladenine, 5-methylpyrimidine (especially, 5-methylcytosine), 5-hydroxymethylcytosine (HMC), glycosyl HMC, gentiobiosyl HMC, 2-aminoadenine, 2-thiouracil, 2-thiothymine, 5-bromouracil, 5-hydroxymethyluracil, 8-azaguanine, 7-deazaguanine, N6-(6-aminohexyl)adenine, 2,6-diaminopurine, etc. Also, the antisense nucleotide may be chemically bonded to one or more moiety or conjugate that improves activity and cell attachment of the antisense nucleotide. The moiety may be an oil-soluble moiety, such as cholesterol moiety, cholesteryl moiety, cholic acid, thioether, thiocholesterol, aliphatic chain, phospholipid, polyamine, polyethylene glycol chain, adamantane acetic acid, palmityl moiety, octadecylamine, and hexylaminocarbonyl-oxycholesterol moiety, but is not limited thereto.

Methods for preparing oligonucleotides having oil-soluble moieties are well known in the related art (U.S. Pat. Nos. 5,138,045, 5,218,105 and 5,459,255). The modified nucleotide may have provide increased stability against nucleases and improved binding ability of the antisense nucleotide to the target mRNA.

The antisense oligonucleotide may be either synthesized in vitro and administered into the body or it may be synthesized in vivo. An example of synthesizing the antisense oligonucleotide in vitro is to use RNA polymerase I. An example of synthesizing the antisense oligonucleotide in vivo is to use a vector having the origin of the multiple cloning site (MCS) in opposite direction so that the antisense RNA is transcribed. Specifically, the antisense RNA may have a translation stop codon within its sequence in order to prevent translation into a peptide sequence.

Design of the antisense oligonucleotide useful in an embodiment of the present invention may be easily performed by the method known in the art with reference to the base sequence of SEQ ID NO:1, 2 or 3 (Weiss, B. (ed.): Antisense Oligodeoxynucleotides and Antisense RNA: Novel Pharmacological and Therapeutic Agents, CRC Press, Boca Raton, Fla., 1997; Weiss, B., et al., Antisense RNA gene therapy for studying and modulating biological processes. Cell. Mol. Life Sci., 55:334-358 (1999)).

As used herein, the term "siRNA" refers to a nucleotide molecule capable of mediating RNA interference (RNAi) or gene silencing (see WO 00/44895, WO 01/36646, WO 99/32619, WO 01/29058, WO 99/07409 and WO 00/44914). Since siRNA can suppress the expression of the target gene, it provides an effective way of gene knockdown or genetic therapy. First discovered in plants, worms, fruit flies and parasites, siRNA has been recently developed and used for studies of mammal cells.

In case the siRNA molecule is used in the present disclosure, it may have a structure in which its sense strand (a sequence corresponding to the NUP153 mRNA sequence) and its antisense strand (a sequence complementary to the NUP153 mRNA sequence) form a double strand. Alternatively, it may have a single-stranded structure having self-complementary sense and antisense strands.

The siRNA is not limited to those in which double-stranded RNA moieties constitute complete pairs, but includes the unpaired moieties such as mismatch (corresponding bases are not complementary), bulge (no base in one chain), etc. The total length of the siRNA may be 10 to 100 bases, specifically 15 to 80 bases, more specifically 20 to 70 bases.

The end of the siRNA may be either blunt or cohesive as long as it is capable of suppressing the expression of the NUP153 gene via RNAi. The cohesive end may be either 3'- or 5'-end.

In the present disclosure, the siRNA molecule may have a short nucleotide sequence (e.g., about 5-15 nucleotides) inserted between the self-complementary sense and antisense strands. In this case, the siRNA molecule formed from the expression of the nucleotide sequence forms a hairpin structure via intramolecular hybridization, resulting in a stem-and-loop structure overall. The stem-and-loop structure is processed in vitro or in vivo to give an activated siRNA molecule capable of mediating RNAi.

According to a certain embodiment of the present invention, the antisense oligonucleotide or siRNA oligonucleotide is a oligonucleotide including a sequence selected from a group consisting of SEQ ID NOs:1, 2, and 3.

According to an embodiment, the inhibitor of NUP153 activity is selected from the group consisting of an aptamer, an antibody, a peptide, a single chain variable region fragment, a low-molecular-weight compound, and a natural extract specifically binding NUP153.

According to another embodiment, the inhibitor of NUP153 activity is selected from the group consisting of an aptamer, an antibody, a peptide, and a single chain variable region fragment specifically binding NUP153.

As used herein, the term "aptamer" refers to an oligonucleotide molecule having a binding affinity for a particular target molecule. The aptamer can also inhibit the activity of a particular target molecule by binding to the particular target molecule. The aptamer of an embodiment of the present invention may be an RNA, a DNA, a modified oligonucleotide or a mixture thereof. The aptamer may be also in a linear or circular form. The length of the aptamer of the embodiment of the present invention is not particularly limited, and may be usually approximately 15 to approximately 200 nucleotides, and may be, for example, approximately 100 nucleotides or less, for example, approximately 30 nucleotides or less, particularly, approximately 60 nucleotides or less, and more particularly, approximately 45 nucleotides or less. The length of the aptamer of the embodiment of the present invention may be, for example, approximately 18, 20 or 25 nucleotides or longer. If the total number of nucleotides is smaller, chemical synthesis, chemical modification, and mass-production will be easier, and there is a major advantage in terms of cost, stability in the body is high, and toxicity is low. The aptamer of the embodiment of the present invention may be prepared by utilizing the SELEX method or an improved version thereof [e.g., Ellington et al., Nature, 346, 818-822 (1990); Tuerk et al., Science, 249, 505-510 (1990)].

The antibody that specifically binds to NUP153 to inhibit its activity is a polyclonal or monoclonal antibody, and for example, a monoclonal antibody. The antibody against NUP153 may be prepared by the typical method known in the art, for example, a fusion method (Kohler and Milstein, *European Journal of Immunology*, 6:511-519 (1976)), a recombinant DNA method (U.S. Pat. No. 4,816,56) or a phage antibody library method (Clackson et al, *Nature*, 352:624-628 (1991) and Marks et al, *J. Mol. Biol.*, 222:58, 1-597 (1991)). The general procedures for antibody production are described in Harlow, E. and Lane, D., Using Antibodies: A Laboratory Manual, Cold Spring Harbor Press, New York, 1999; Zola, H., *Monoclonal Antibodies: A Manual of Techniques*, CRC Press, Inc., Boca Raton, Fla., 1984; and Coligan, *Current Protocols In immunology*, Wiley/Greene, N.Y., 1991, which are incorporated herein by references. For example, the preparation of hybridoma cell lines for monoclonal antibody production is done by fusion of an immortal cell line and the antibody-producing lymphocytes. This can be done by techniques well known in the art. Polyclonal antibodies may be prepared by injection of the NUP153 antigen to suitable animal, collecting antiserum containing antibodies from the animal, and isolating specific antibodies by any of the known affinity techniques.

In the present invention, the antibody may include a single-chain variable fragment (scFv). The single-chain variable fragment may consist of "light chain variable region (VL)-linker-heavy chain variable region (VH)". The linker means an amino acid sequence having a predetermined length, which functions to artificially link the variable regions of heavy and light chains.

The peptide that specifically binds to NUP153 to inhibit its activity may be obtained by the typical method known in the art, for example, by phage display (Smith G P, "Filamentous fusion phage: novel expression vectors that display cloned antigens on the virion surface". Science 228 (4705): 1315-1317 (1985); Smith G P, Petrenko V A, "Phage display". Chem. Rev. 97 (2):391-410 (1997)).

The low-molecular-weight compound inhibiting NUP153 activity may be easily obtained by the screening method described below.

According to an embodiment of the present invention, the inhibitor of NUP153 activity recognizes an epitope in SEQ ID NO:4. According to another embodiment of the present invention, the inhibitor of NUP153 activity recognizes an epitope in the amino acid sequences 245-326 of SEQ ID NO:4.

The inhibitor of NUP153 gene expression or NUP153 activity effectively inhibits angiogenesis through the mechanism of inhibiting invasion and tube formation, whereby it may be effectively used for preventing or treating an angiogenic disease.

The angiogenic diseases mean diseases caused by formation of blood vessel, for example, the angiogenic disease include, but are not limited to, cancers, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, and rodegenerative diseases.

According to another embodiment of the present invention, the angiogenic disease of an embodiment of the present invention is selected from the group consisting of cancers, diabetic retinopathy, retinopathy of prematurity, corneal graft rejection, neovascular glaucoma, erythema, and proliferative retinopathy. According to a certain embodiment of the present invention, the angiogenic disease of the present invention is selected from the group consisting of diabetic retinopathy, retinopathy of prematurity, corneal graft rejection, neovascular glaucoma, erythema, and proliferative retinopathy. According to a certain embodiment of the present invention, the angiogenic disease of the present invention is selected from the group consisting of diabetic retinopathy, retinopathy of prematurity, and proliferative retinopathy.

According to an embodiment of the present invention, the inhibitor of NUP153 gene expression or NUP153 activity reduces export of mRNA of a pro-angiogenic factor from nucleus. According to another embodiment of the present invention, the pro-angiogenic factor is selected from the group consisting of VEGF, HGF, and bFGF.

According to an embodiment of the present invention, the pharmaceutical composition including inhibitors of NUP153 gene expression or NUP153 activity may contain pharmaceutically acceptable carriers. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to.

The pharmaceutical composition according to an embodiment of the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to an embodiment of the present invention may be orally or parentally administered. When the pharmaceutical composition of an embodiment of the present invention is administered parenterally, it can be done by intravenous, subcutaneous, intramuscular, abdominal or transdermal administration.

A suitable dosage amount of the pharmaceutical composition of an embodiment of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, suitable dosage unit for human host is to administer with the pharmaceutical composition in 0.001-1000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further include dispersant or stabilizer.

In another aspect of the present invention, there is provided a method for preventing or treating an angiogenic disease, including administering to a subject in need thereof an inhibitor of NUP153 (nucleoporin 153 kDa) gene expression or NUP153 activity.

Since the method for preventing or treating an angiogenic disease of the present invention follows the diseases, the related transcription factor (NUP153), and the related gene (NUP153 gene) of the present pharmaceutical composition described above, the common descriptions between them are omitted in order to avoid undue redundancy leading to the complexity of this specification.

In still another aspect of the present invention, there is provided a method for screening an agent for preventing or treating angiogenic diseases including the following steps:

(a) contacting a test material with a cell including NUP153 gene or NUP153; and (b) measuring an amount of NUP153 gene expression or NUP153, or an activity of the NUP153;

Wherein where down-regulation of the amount of NUP153 gene expression or NUP153, or the activity of NUP153 is observed compared to a non-treatment of the test material, the test material is determined as an agent for preventing or treating angiogenic diseases.

In the screening method of the present invention, the screening of angiogenesis inhibitor suppressing NUP153 activity is performed by screening a material that inhibits the activity of NUP153 or binds to NUP153. In this case, any form of NUP153 including a separated form and intracellular form of NUP153 may be used.

The screening method of the present invention may be carried out by various processes, especially by a high throughput method through diverse binding assays known to those skilled in the art.

In the screening method of the present invention, the test material or NUP153 may be labeled with a detectable label. For example, the detectable label includes, but is not limited to, a chemical label (e.g., biotin), an enzyme label (e.g., horseradish peroxidase, alkaline phosphatase, peroxidase, luciferase, β-galactosidase and β-glucosidase), a radioactive label (e.g., C14, I125, P32 and S35), a fluorescence label (e.g., coumarin, fluorescein, FITC (fluoresein Isothiocyanate), rhodamine 6G, rhodamine B, TAMRA (6-carboxytetramethyl-rhodamine), Cy-3, Cy-5, Texas Red, Alexa Fluor, DAPI (4,6-diamidino-2-phenylindole), HEX, TET, Dabsyl and FAM), a luminescent label, a chemiluminescent label, FRET (fluorescence resonance energy transfer) label or a metal label (e.g., gold and silver).

For using the detectably labeled NUP153 or test material, a binding of NUP153 with the test material may be analyzed through the signal generated by the label. If alkaline phosphatase is used as a label, bromo-chloro-rndolylphosphate (BCIP), nitro blue tetrazolium (NBT), naphthol-AS-B1-phosphate and ECF (enhanced chemifluorescence) may be used as a substrate. If horseradish peroxidase is used as a label, chloronaphtol, arainoethylcarba zol, diaminobenzidine, D-luciferin, lucigenin (bis-N-raethylacridinium nitrate), resorufin benzyl ether, luminol, Amplex Red reagent (10-acetyl-3,7-dihydroxyphenoxazine), HYR (p-phenylenediamine-HCL and pyrocatecbol), TMB (tetramethylbenzidine), ARTS (2,2'-Azine-di[3-ethylbenzthiazoline sulfonate]), OPB (o-phenylenediarivine) and naphtol/pyronin may be used as a substrate.

Alternatively, the binding of NUP153 with the test material may be measured without the labeling of the interactants. For example, a microphysiometer may be used to analyze the binding of NUP153 with the test material. The microphysiometer is a device for determining the cell's environment-acidifying rate using LAPS (light-addressable potentiometric sensor). The change of acidifying rate may be used as an indicator for the binding of Prx II protein with the test material (McConnell et al., *Science* 257:1906-1912 (1992)).

The binding capacity of the test material to NUP153 may be determined by real-time BIA (bimolecular interaction analysis) (Sjolander & Urbaniczky, *Anal. Chem.*, 63:2338-2345 (1991), and Szabo et al., *Curr. Opin. Struct. Biol.* 5:699-705 (1995)). BIA is a real-time analyzing technique for the specific interaction without the labeling of interactants (e.g., BIAcore™). The change of SPR (surface plasraon resonance) is used as an indicator of real-time reaction between the molecules.

Further, the screening method of the present invention may be performed according to a two-hybrid or three-hybrid method (U.S. Pat. No. 5,283,317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and WO 94/10300). In this case, NUP153 can be used as a "bait" protein. According to this method, a substance, in particular, a protein binding to NUP153 can be screened. The two-hybrid system is based on the modularity of transcription factors that consist of splittable DNA-binding and activating domains. Briefly, this technique employs two DNA constructs. For example, in one construct, a NUP153-encoding polynucleotide is fused with a DNA binding domain-encoding polynucleotide of a known transcription factor (e.g., GAL-4). In the other construct, a DNA sequence encoding the protein to be analyzed ("prey" or "sample") is fused with a polynucleotide encoding the activating domain of the known transcription factor. When the bait and the prey interact to form a complex in vivo, the DNA-binding and activating domains of the transcription factor are brought in proximity and transcription of reporter genes (e.g., LacZ) occur. The detection of the expression of the reporter gene confirms that the analyte protein binds with the NUP153, meaning that it can be utilized as an angiogenesis inhibitor.

According to the method of the present invention, first, the test material to be analyzed is contacted with a cell including NUP153 gene or NUP153.

In the context related to the screening method of the present invention, the term "test material" refers to an unknown substance which is screened to test whether it affects the amount of NUP153 gene expression or NUP153, or the activity of NUP153.

The test material may be a chemical, a peptide, an antisense-RNA, a siRNA (small interference RNA) or a natural extract, but is not limited thereto.

The test sample analyzed by the screening method of the present invention may be an individual compound or a mixture of compounds (e.g., natural extract, or cell or tissue culture). The test material may be obtained from a library of synthetic or natural compounds. The method for obtaining the library of such compounds is known in the art. A library of synthetic compounds is commercially available from Maybridge Chemical Co. (UK), Comgenex (USA), Brandon Associates (USA), Microsource (USA) and Sigma-Aldrich (USA), and a library of natural compounds is commercially available from Pan Laboratories (USA) and MycoSearch (USA).

The test material may be obtained through various known combinational library methods. For example, it may be acquired by a biological library method, a spatially-addressable parallel solid phase or solution phase library method, a synthetic library method requiring deconvolution, a "1-bead/1-compound" library method, and a synthetic library method using affinity chromatography selection. The methods for obtaining the molecular libraries are described in DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 12 33, 1994.

Subsequently, an amount of NUP153 gene expression or NUP153, or an activity of NUP153 treated with the test material is measured. If down-regulation of the amount of NUP153 gene expression or NUP153, or the activity of NUP153 is observed as the result thereof, the test material may be decided as an agent for preventing or treating angiogenic diseases.

If the screening method of the present invention is performed by analyzing the expression of NUP153 gene, the measurement of the expression level of NUP153 gene can be carried out by a variety of methods known in the art. For example, RT-PCR (Sambrook et al., Molecular Cloning. A laboratory Manual, 3rd ed. Cold Spring Harbor Press (2001)), Northern blotting (Peter B. Kaufma et al., *Molecular and Cellular Methods in Biology and Medicine*, 102-108, CRC press), hybridization using cDNA microarray (Sambrook et al., Molecular Cloning. A Laboratory Manual, 3rd ed. Cold Spring Harbor Press (2001)) or in situ hybridization (Sambrook et al., Molecular Cloning, A Laboratory Manual, 3rd ed. Cold Spring Harbor Press (2001)) may be used.

If the analysis is performed according to RT-PCT protocol, total RNA is first isolated from cells treated with a test material to be analyzed, and a first cDNA strand is then synthesized using oligo dT primer and reverse transcriptase. Then, PCR amplification is performed using the first cDNA strand, as a template and a NUP153 gene-specific primer set. For example, the NUP153 gene-specific primer set is SEQ ID NO:3 and SEQ ID NO:4. Finally, the PCR amplified products are resolved by electrophoresis and bands are analyzed for assessing the expression level of the NUP153 gene.

The change in the amount of the NUP153 may be measured by various techniques known in the art. For example, the change in the amount may be measured by various immunoanalysis formats using antibodies specifically binding NUP153.

The immunoassay may be performed by a variety of quantitative immunoassay protocols known in the art. The immunoassay format includes, but is not limited to, radioimmunoassay analysis, radioactive immunoprecipitation, immunoprecipitation, immunohistochemical staining, ELISA (enzyme-linked immunosorbent assay), Capture-ELISA, sandwich assay, immunofluorescence and immune affinity purified. The immunoassay or the immuno staining method is described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Laboratory Press, 1999 and the literatures are inserted as reference in herein.

For example, when the method of the present disclosure is performed using radioimmunoassay analysis, the antibody labeled with radioactive isotopes (e.g., C14, I125, P32 and S35) may be used for detecting a marker of the present invention.

When the method of the present disclosure is performed using the ELISA, certain examples of the present invention include: (i) coating unknown cell cytolysate samples of interest for analysis on the surface of a solid substrate; (ii) contacting the cell cytolysate with NUP153-specific antibody for the marker as the primary antibody; (iii) contacting the resultant of step (ii) with the secondary antibody conjugated enzyme; and (iv) detecting the enzyme activity.

The appropriate solid substrate is hydrocarbon polymers (e.g., polystyrene and polypropylene), glass, metal, or gel, and, for example, a micro-titer plate.

The appropriate secondary antibody conjugated enzyme includes, but is not limited to, color-developing reaction, fluorescent reaction, luminescent reaction or infrared reaction, for example, alkaline phosphatase, β-galactosidase, horseradish peroxidase, luciferase and cytochrome P450. Where alkaline phosphatase is used for the enzyme binding to the secondary antibody, bromochloroindolylphosphate (BCIP), nitro blue tetrazolium (NBT), naphthol-AS-B1-phosphate and ECF (enhanced chemifluorescence) may be used as a substrate for color-developing reactions. In the case of using horseradish peroxidase, chloronaphtol, aminoethylcarbazol, diaminobenzidine, D-luciferin, lucigenin (bis-Nmethylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine may be used as a substrate; and in the case of using glucose oxidase, t-NBT (nitroblue tetrazolium) or m-PMS (phenzaine methosulfate) may be used as a substrate.

When the method of the present disclosure is performed using the Capture-ELISA, certain examples of the present invention include the steps of: (i) coating the antibody for the marker as capturing antibody on the surface of a solid substrate; (ii) contacting the sample with the capturing antibody; (iii) contacting the resultant of step (ii) with the detecting antibody which is combined with label generating signal and react specifically to the NUP153; and (iv) detecting the signal from the label.

The detecting antibody has the label generating detectable a signal. The label includes, but is not limited to, chemical (e.g., biotin), enzyme (alkaline phosphatase, β-galactosidase, horseradish peroxidase and cytochrome P450), radioactive material (e.g., C14, I125, P32 and S35), fluorescent material (e.g., fluorescein), luminescent material, chemiluminescent material and FRET (fluorescence resonance energy transfer). A variety of labels and labeling methods are described in Ed. Harlow and David Lane, Using Antibodies: A Laboratory Manual, Cold Spring Harbor Laboratory Press, 1999.

The final measurement of enzyme activity or measurement of the signal may be carried out in accordance with a variety of methods known in the art. The detection of this signal permits to quantitative analysis of NUP153. In the case of using biotin as label, the signal is easily detected using streptavidin. In the case of using luciferase as label, the signal is easily detected using luciferin.

Wherein where down-regulation of the amount of NUP153 gene expression or NUP153, or the activity of NUP153 is observed compared to a non-treatment of the test material, the test material is determined as an agent for preventing or treating angiogenic diseases.

The low signal was seen in the test material-treated sample, compared to the non-treated sample, indicating that the test material may be a candidate of an agent for preventing or treating angiogenic diseases.

According to an embodiment of the present invention, the NUP153 includes the amino acid sequences 245-326 of SEQ ID NO:4. According to another embodiment of the present invention, the NUP153 includes the amino acid sequences of SEQ ID NO:4.

Since the method for screening an agent for preventing or treating angiogenic diseases of the present invention follows the diseases, the related transcription factor (NUP153), and the related gene (NUP153 gene) of the present pharmaceutical composition described above, the common descriptions between them are omitted in order to avoid undue redundancy leading to the complexity of this specification.

The features and advantages of the present invention will be summarized as follows:

(a) The present invention provides a pharmaceutical composition for preventing or treating angiogenic diseases including inhibitors of NUP153 gene expression or NUP153 activity as active ingredient and a method for screening an agent for preventing or treating angiogenic diseases.

(b) According to the present invention, inhibition of the NUP153 gene expression or the NUP153 activity reduces export of mRNA of a pro-angiogenic factor (VEGF, HGF and bFGF) from nucleus.

(c) In addition, inhibition of the NUP153 gene expression or the NUP153 activity has effect that angiogenesis are inhibited by inhibition of invasion and tube formation in a dose-dependent manner without showing toxicity.

(d) Therefore, the pharmaceutical composition of the present invention may be used for preventing or treating a variety of angiogenesis-related diseases, and the method for screening of the present invention may be valuably used in finding a new agent for preventing or treating angiogenic diseases.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Test Animals

C57BL/6 mice were purchased from Samtako (Korea). Care, use, and treatment of all animals in this study were in strict agreement with the ARVO statement for the Use of Animals in Ophthalmic and Vision Research.

Compounds

OMe-Syn was purified from a plant of the Rutaceae family by our group (Kim et al., *Biochem. Biophys. Res. Commun* 399, 20-23 (2010)) as well as a biotinylated analogue of OMe-Syn was synthesized.

Synthesis of a Biotinylated Analogue of OMe-Syn

NHS-biotin was purchased from Thermo Scientific (USA). NMR Spectrum was measured at 30° C. by Varian Inova 600 MHz Spectrometer (International Equipment Trading Ltd., USA). High resolution mass spectra were acquired on a Bruker Daltonics Apex III 4.7e Fourier-transform mass spectrometer equipped with an Apollo API source. A Betasil C18 column (5 mm, 150×21.2 mm) and Phenomenex Luna column (C18, 3 μm, 2.0 mm×150 mm) is used in HPLC and LC-MS analysis, respectively. Every solvent of reaction and chromatography was Omnisolv HPLC grade solvents, and Millipore Milli-Q PF filtered $H_2O$ was used.

NHS-biotin (20 mg) was added to R-(−)-β-O-Methylsynephrine (OMe-Syn) solution in methanol (3 mL). The reaction was monitored by LC-MS after adjusting pH 8 by adding sodium hydroxide (0.2M) and stirring at RT for 5 hr. After the reaction was complete, the reaction solvent was evaporated. The crude product chromatography was done by using Betasil C18 column (5 mm, 150×21.2 mm), 100% MeOH in 100% $H_2O$ for 50 min at a flow rate of 10 mL/min (yield: 90% at retention time 23 min): 1HNMR (600 MHz, DMSO-d6, δH), 7.12 (d, 2H, J=8), 6.77 (d, 2H, J=8), 6.42 (s 1H), 6.36 (s, 1H), 4.27 (m, 1H), 4.24 (t, 1H, J=7), 4.14 (m, 1H), 3.56 (dd, 1H, J=8.2, 4.6), 3.39 (m, 2H), 3.10 (s, 3H), 2.85 (m, 2H), 2.81 (s, 3H), 2.22 (m, 2H), 1.61 (m, 2H), 1.45 (m, 2H), 1.30 (m, 2H). 13CNMR (600 MHz, DMSO-d6, δC), 172.3, 162.8, 157.2, 129.8, 127.9 (2C), 115.3 (2C), 80.9, 61.1, 59.2, 56.1, 55.5, 53.6, 40.0, 36.7, 33.8, 32.4, 28.3, 24.8; (+)HRESIMS m/z 408.1957[M+H]+(calcd for $[C_2OH_3ON_3O_4S_1]+$, 408.1951, Δ1.47 ppm).

Cell Culture and Proliferation Assay

HUVECs (7-11 passages) were grown in EGM-2 medium supplemented with 10% FBS. The cells were maintained at 37° C. in a humidified 5% $CO_2$ incubator. Cell proliferation assay conducted using 3-(4,5-dimethylthiazol-2-yl)-2,5-diphenyltetrazolium bromide (MTT) colorimetric assay and cytotoxicity was carried out using Trypan blue exclusion assay.

Capillary Tube Formation Assay

Matrigel (10 mg/mL) was coated in a 48-well plate and polymerized for 1 hour at 37° C. The HUVECs (6×10⁴ cells) were seeded on the surface of the Matrigel in a 48-well plate. Then conditioned medium (CM) of NUP153-knockdown HeLa cells (Human cervical carcinoma) were added for 4-16 hours at 37° C. The morphological changes of the cells and tubular structure formed were observed under a microscope (IX71, Olympus) and photographed at a 100× magnification with a camera (DP70, Olympus).

Chemo-Invasion Assay

To examine the invasiveness of HUVECs in vitro, the present inventors used a Transwell chamber (Corning Costar, Corning, N.Y.) system with 8.0-μm pore polycarbonate filter inserts (Cheong et al., Cancer Res. Treat 43, 124-130 (2011)). Briefly, the lower side of the filter was coated with gelatin (10 mL, 1 mg/mL) and the upper side was coated with Matrigel (10 μL, 3 mg/mL). The CM of NUP153-knockdown HeLa cells were added to the lower chamber and HUVECs ($7 \times 10^4$ cells) were placed in the upper chamber of the filter. The chamber was incubated at 37° C. for 18 h, and then the cells were fixed with 70% methanol and stained with hematoxylin and eosin. The invasiveness of cells was measured by counting the number of whole cells in the lower side of the filter using a microscope at 100× magnification, and cells were photographed at 100× magnification.

Phage Display Affinity Selection

Biotinyl-OMe-Syn was immobilized onto a streptavidin-coated plate (Pierce Biotechnology Inc., Rockford, Ill.), and phage display was performed using T7 phages encoding human cDNA libraries from colon tumor, lung tumor and heart tissues (Novagen Inc., Madison, Wis.) as described previously (Shim et al., Chem. Biol 11, 1455-1463 (2004)). Specific OMe-Syn binding phages were isolated and analyzed by DNA sequencing. The sequence homologies of the obtained sequences were compared with sequences in GenBank™ using the BLAST program.

Molecular Cloning, Expression and Purification of N-Terminus Partial Domain of NUP153 Protein To obtain the recombinant NUP153 protein from bacteria, a PCR-amplified N-terminus (amino acids 235-326) cDNA of NUP153 (NM_005124) was into the EcoRI/SalI site of pET-28a expression vector (Novagen, Billerica, Mass.). Rosetta™ (DE3) E. coli strains were transformed with the plasmid and N-terminus partial domain of NUP153 protein was purified using Ni-NTA agarose bead (Quiagen, Hilden, Germany). Bead bound protein was eluted with elution buffer containing high concentration of imidazole according to the manufacturer's instructions.

Surface Plasmon Resonance (SPR) Analysis

Biotin and biotinylated OMe-Syn were sequentially immobilized on the surface of a streptavidin-coated sensor chip. Molecular interaction analysis was performed using the BIAcore 2000 (BIAcore AB) as described previously (Shim et al., Chem. Biol 11, 1455-1463 (2004)). The SPR response curves were analyzed with BIAcore Evaluations software, version 3.1. The apparent association and dissociation constants were calculated from the kinetic constants equations: $K_A = k_a/k_d$, $K_D = k_d/k_a$ Western Blot Analysis The cell lysates were separated by 10% SDS-PAGE and were then transferred to PVDF membranes (Millipore, Bedford, Mass.) using standard electroblotting procedures. The blots were then blocked and immunolabeled overnight at 4° C. with anti-NUP153 (Abcam, Cambridge, Mass.), anti-VEGF (Abcam, Cambridge, Mass.), anti-bFGF (Abcam, Cambridge, Mass.), anti-HGF (Abcam, Cambridge, Mass.) and anti-tubulin (Upstate Biotechnology Inc. Lake Placid, N.Y.) primary antibodies. Immunolabeling was detected by an ECL kit (Amersham Biosciences Inc., Buckinghamshire, UK) according to the manufacturer's instructions.

RNA Interference of NUP153

Human NUP153 specific siRNA(CCACCG-CAACAAGCCCAGTAGTTTA, SEQ ID NO:1) was constructed using the Stealth™ RNA interference (Invitrogen, Grand Island, N.Y.). For the knockdown of NUP153 mRNA, HUVECs were transfected with either control or NUP153 siRNA (1, 10 nM) using the Lipofectamine™ 2000 transfection reagent (Invitrogen, Grand Island, N.Y.) according to the manufacturer's instructions.

Morpholinos of NUP153 and OMe-Syn Treatment to Zebrafish

Zebrafish were maintained on 14 hours light/dark cycle at 28° C. All experiments involving zebrafish were performed according to the National Institute of Health guidelines. Embryos were collected and raised in Ringer's solution according to standard protocol (Westerfield, 1995). Zebrafish were injected in Ringer's solution at the one-cell stage with morpholino oligonucleotides (MO). MO was obtained from Gene Tools (Philomath, Oreg.) with the following sequence to block 5' translation of NUP153: 5'-TTTTCCCTCCTCCTGTCGCCGCCAT-3' (SEQ ID NO:2) and splicing of NUP153: 5'-ACATTGAGACATGT-TCAGACCTGAT-3' (SEQ ID NO:3), respectively. DMSO and OMe-Syn stock solution (10 mM in DMSO) were dissolved in ringer's solution to appropriate concentrations. Final volume of compounds did not exceed 1% of the total volume. Embryos were added to the solutions at one cell stage. Tricaine supplied in Ringer's solution (0.6%, w/v) was used to anesthetize the embryos for imaging. Microscopy images of zebrafish were taken with Fluoview FV1000, Olympus.

Oxygen-Induced Retinopathy

OIR was induced as described by Smith et al. (Smith et al., Invest. Ophthalmol. Vis. Sci 35, 101-111 (1994)) with some modifications (Zhang et al., Diabetologia 44, 757-765 (2001)). Briefly, newborn mice were arbitrarily assigned to experimental and control groups. At postnatal day 7 (P7), pups (8-10 pups) in the experimental group were exposed to hyperoxia (75±0.5% 02) for 5 days (P7-P12) and then returned to normoxia (room air) for 6 days. Neovascularization occurs upon return to normoxia and peaks at P17. To assess the anti-angiogenic activity of OMe-Syn, the pups were injected intravitreously with 20 μM OMe-Syn in 1 μL PBS on P14, when maximum retinal neovascularization began.

Quantitative Assessment of Retinal Neovascularization by Counting Vascular Lumens At P17, the eyes were removed, fixed in 4% paraformaldehyde in 0.1 M phosphate buffer for 24 hours, and embedded in paraffin. Sagittal sections of 5 μm, each 30 μm apart, were cut through the cornea parallel to the optic nerve. The sections were stained with hematoxylin and eosin to assess retinal vasculature via light microscopy (Carl Zeiss, Chester, Va., USA). Any vascular lumens on the vitreal side of the inner limiting membrane were counted in at least 10 sections from each eye by two independent observers blind to treatment. The average intravitreal vessels/section was calculated for each group. There were at least six animals in each group.

Statistical Analysis

Results are expressed as the mean±standard error (SE). Student's t-test was used to determine statistical significance between control and test groups. A p-value of <0.05 was considered statistically significant.

Results

OMe-Syn Inhibits ISV Angiogenesis in Fli1a:EGFP Transgenic Zebrafish Embryos

Figure 1E:
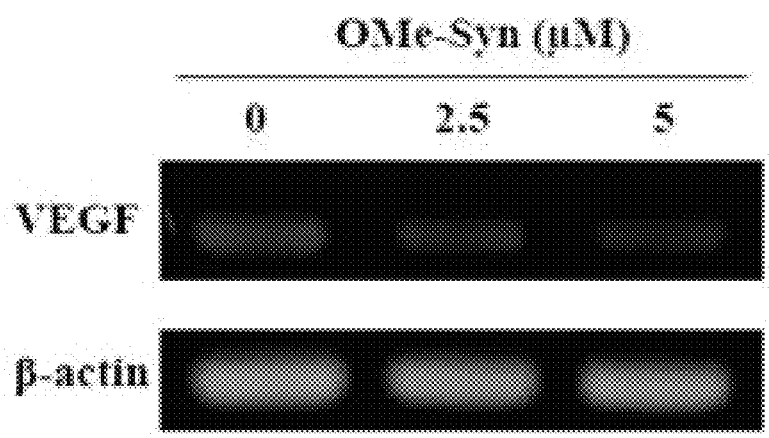

The present inventors previously reported that OMe-Syn, an anti-angiogenic small molecule, inhibited VEGF-induced angiogenesis in vitro and in vivo (Kim et al., Biochem. Biophys. Res. Commun 399, 20-23 (2010)). The anti-angiogenic activity of OMe-Syn was further investigated using fli1a:EGFP transgenic zebrafish, a well-established model organism for studying angiogenesis through visualization of blood vessel development. Notably, OMe-Syn treatment in zebrafish embryos (n=30) effectively inhibited angiogenesis, resulting in a decreased number of complete intersegmental vessels (ISVs) in a dose-dependent manner, at 30 hours post fertilization (hpf) without compromising the viability of the animals (FIGS. 1A to 1D). The VEGF mRNA level of OMe-Syn-treated embryos was also reduced compared with dimethyl sulfoxide (DMSO)-treated controls (n=30) (FIG. 1E). These data clearly demonstrated that the natural small molecule OMe-Syn inhibits angiogenesis in a zebrafish model and is a useful chemical tool for studying angiogenesis.

OMe-Syn Binds to the N-Terminal Domain of NUP153

Figure 2A:
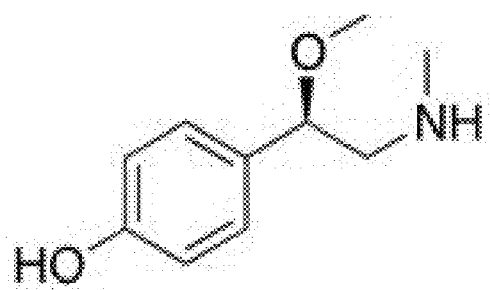
FIGS. 2A through 2E represent identification of OMe-Syn-binding protein using phage display biopanning.
Figure 2B:
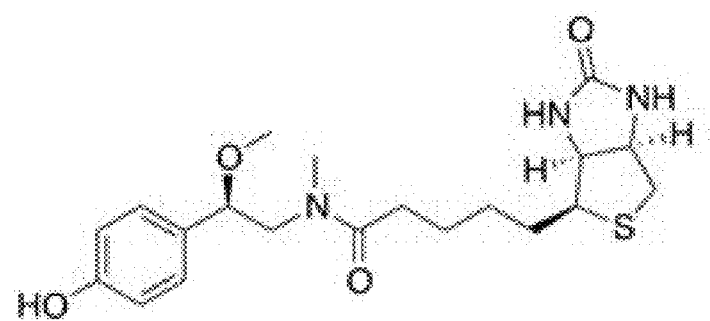
Figure 2C:
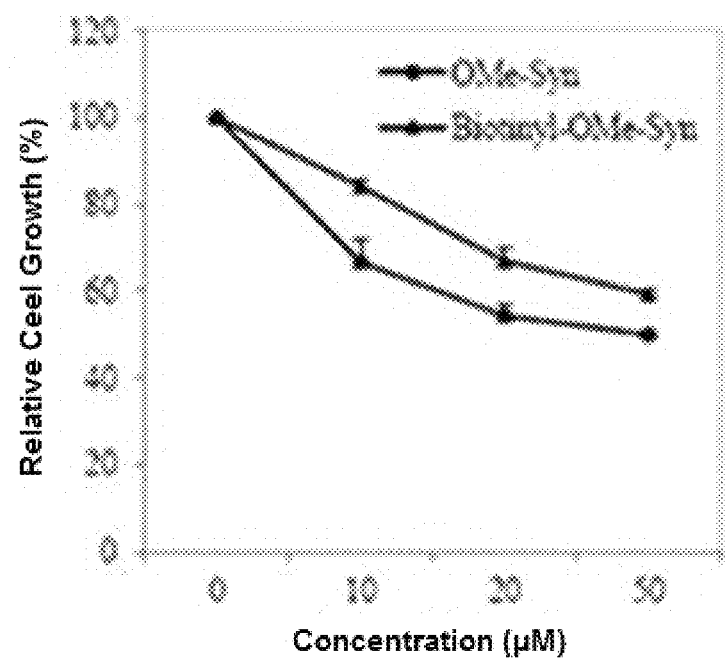
Figure 2D:
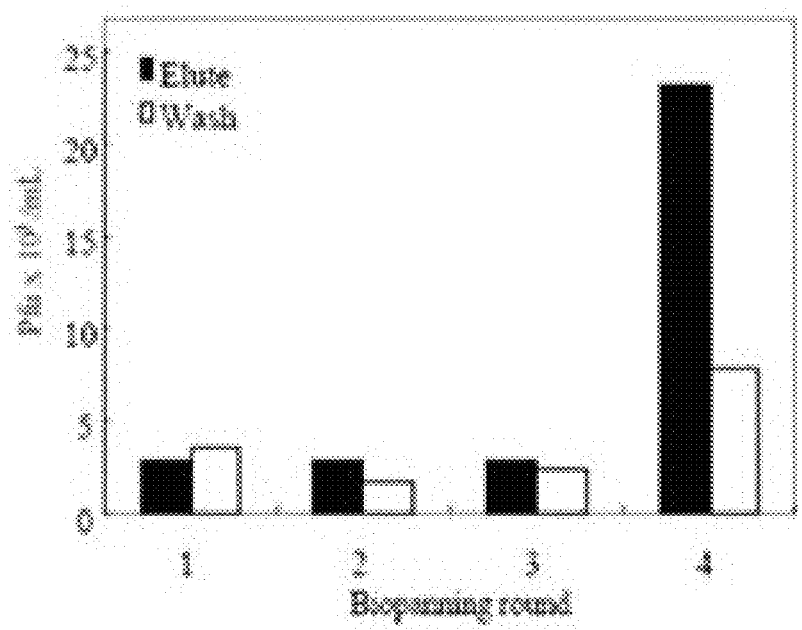
Figure 2E:
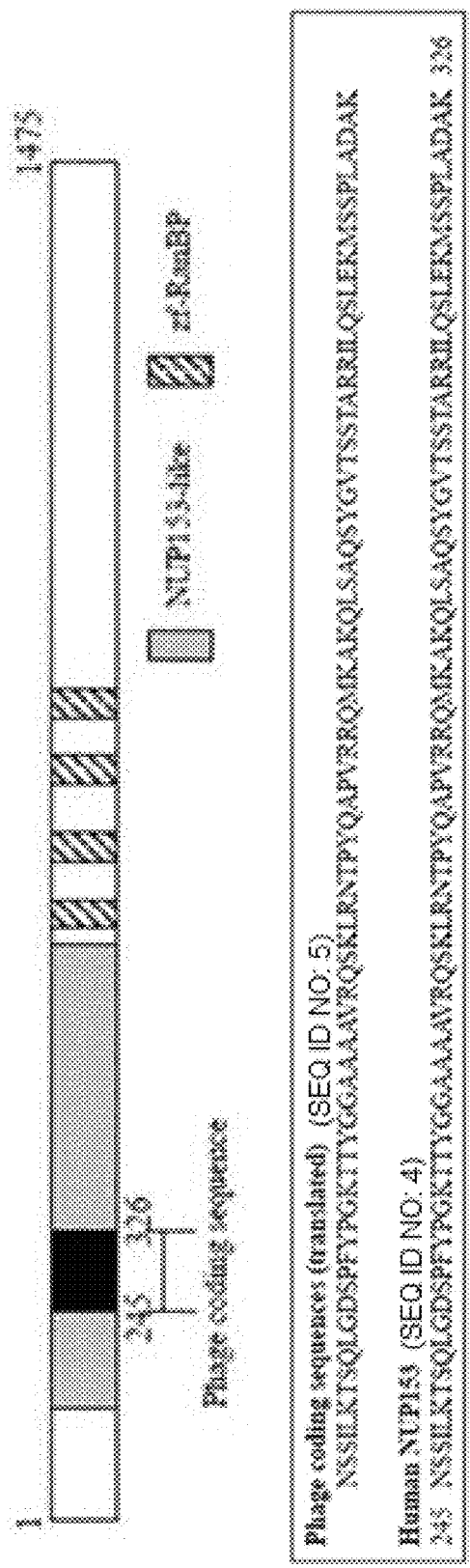
Figure 3A:
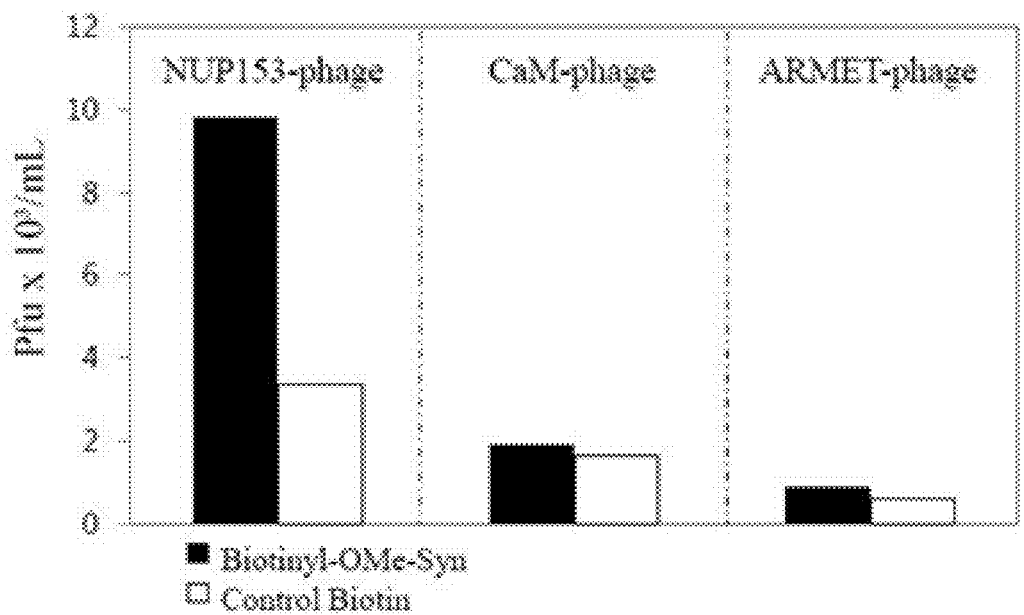
FIGS. 3A to 3D represent validation of the interaction of OMe-Syn and NUP153.

OMe-Syn has a unique chemical structure that is distinct from known angiogenesis inhibitors and exhibits potent anti-angiogenic activity in vitro and in vivo. Thus, investigation of its mechanisms of action allows to gain new understanding of, and control over, angiogenesis (FIG. 2A). First, the present inventors synthesized biotinylated OMe-Syn (biotinyl-OMe-Syn) as an affinity probe (FIG. 2B) and evaluated the bioactivity of the synthesized probe. Biotinyl-OMe-Syn inhibited the proliferation of human umbilical cord vein endothelial cells (HUVECs) in a dose-dependent manner similar to that using OMe-Syn (FIG. 2C), validating the biological activity of the biotinylated derivative of OMe-Syn. Next, phage display biopanning was performed using biotinyl-OMe-Syn. T7 phages encoding human cDNA libraries (1×10$^9$ pfu/mL) from colon tumor, lung tumor, and heart tissue were used as expressed proteomes for the identification of OMe-Syn binding proteins. After the fourth round of biopanning (FIG. 2D), plaques were selected randomly, and their DNA inserts were sequenced and characterized. Interestingly, two of the isolated clones had an open reading frame (ORF) of 82 amino acids identical to the N-terminal region of human nucleoporin 153 kDa (NUP153). In particular, the compound interacted with the RNA binding domain (RBD) within the N-terminal region of NUP153 (FIG. 2E). The other 16 phage clones were also analyzed using the basic local alignment search tool (BLAST) system. The other proteins identified were calmodulin (CaM), mesencephalic astrocyte-derived neurotrophic factor precursor (ARMET), Sjogren's syndrome/scleroderma autoantigen 1, isoform CRA, and putative p150. Detailed DNA sequences of these phage clones are shown in Table S1. Among these candidate proteins, the NUP153-expressing phage specifically bound to OMe-Syn in the phage binding assay but not to biotin. Other binding protein-expressing phages of OMe-Syn did not bind to OMe-Syn as shown in FIG. 3A, suggesting these phages expressed a non-coding sequence or a misfolded protein. Furthermore, in a phage competition assay, pre-incubation with OMe-Syn and NUP153-expressing phage blocked the binding of the phage to immobilized OMe-Syn in a dose-dependent manner (FIG. 3B), demonstrating the specific binding of OMe-Syn to NUP153. Accordingly, further investigation focused on NUP153 as a target binding protein of OMe-Syn.

Validation of OMe-Syn Binding to NUP153 In Vitro

Figure 3B:
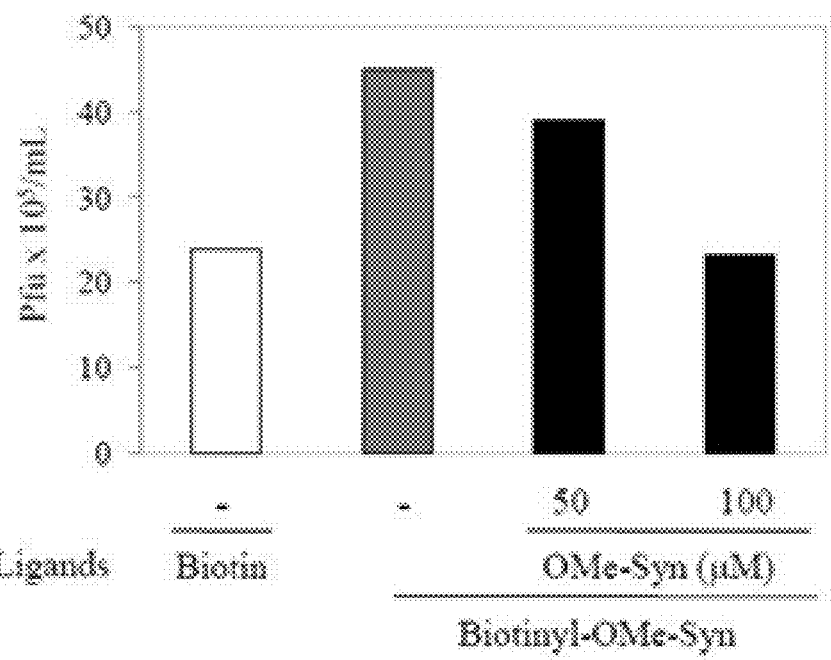
Figure 3C:
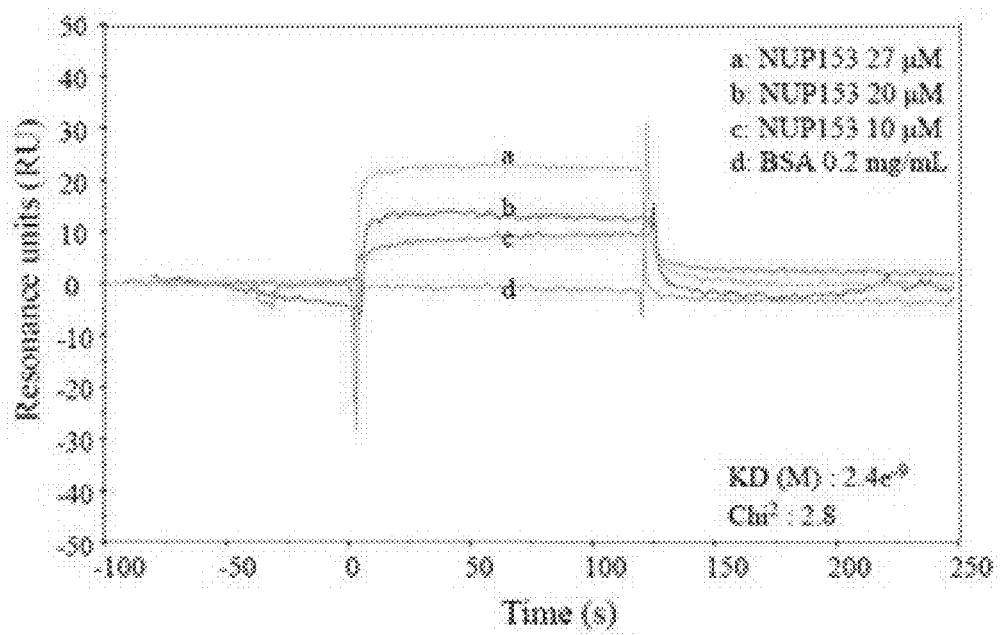

To examine the binding affinity of OMe-Syn to NUP153, the N-terminal partial domain of NUP153, which corresponds to phage coding sequences (FIG. 2E), was cloned and expressed in *Escherichia coli*. The cloning and purification of recombinant NUP153 is described in the experimental procedures. Using this purified N-terminal partial domain of NUP153, surface plasmon resonance (SPR) analysis was conducted at various concentrations of the protein (10-27 μM). Notably, purified NUP153 bound to OMe-Syn dose dependently, and the apparent dissociation constant (Kd) was 2.4×10$^{-9}$M (FIG. 3C).

The difference in amino acid composition properties between the full sequence of NUP153 and isolated domain of NUP153 from phage display was also analyzed (Table 1). Notably, the isolated domain of NUP153 from phage display showed higher aliphatic and basic properties, whereas the acidity was decreased (Table 2).

TABLE 1

| Residue | NUP153 Number | NUP153 Mole % | Isolated domain of NUP153 from phage display Number | Isolated domain of NUP153 from phage display Mole % |
|---|---|---|---|---|
| A = Ala | 99 | 6.7 | 10 | 12.2 |
| D = Asp | 42 | 2.8 | 2 | 2.4 |
| E = Glu | 72 | 4.9 | 1 | 1.2 |
| F = Phe | 89 | 6.0 | 1 | 1.2 |
| G = Gly | 127 | 8.6 | 5 | 6.1 |
| H = His | 11 | 0.7 | 0 | 0.0 |
| I = Ile | 45 | 3.1 | 2 | 2.4 |
| K = Lys | 97 | 6.6 | 7 | 8.5 |
| L = Leu | 69 | 4.7 | 7 | 8.5 |
| M = Met | 15 | 1.0 | 2 | 2.4 |
| N = Asn | 68 | 4.6 | 2 | 2.4 |
| P = Pro | 117 | 7.9 | 5 | 6.1 |
| Q = Gln | 58 | 3.9 | 7 | 8.5 |
| R = Arg | 41 | 2.8 | 6 | 7.3 |
| S = Ser | 267 | 18.1 | 12 | 14.6 |
| T = Thr | 133 | 9.0 | 6 | 7.3 |
| V = Val | 77 | 5.2 | 3 | 3.7 |
| W = Trp | 7 | 0.5 | 0 | 0.0 |
| Y = Tyr | 13 | 0.9 | 4 | 4.9 |
| C = Cys | 28 | 1.9 | 0 | 0.0 |

TABLE 2

| Property | Residues | NUP153 Number | NUP153 Mole % | Isolated domain of NUP153 from phage display Number | Isolated domain of NUP153 from phage display Mole % |
|---|---|---|---|---|---|
| Aliphatic | (A + I + L + V) | 290 | 19.7 | 22 | 26.8 |
| Aromatic | (F + H + W + Y) | 120 | 8.1 | 5 | 6.1 |
| Non-polar | (A + F + G + I + L + M + P + V + W + Y) | 658 | 44.6 | 39 | 47.6 |
| Polar | (D + E + H + K + N + Q + R + S + T) | 789 | 53.5 | 43 | 52.4 |
| Charged | (D + E + H + K + R) | 263 | 17.8 | 16 | 19.5 |
| Basic | (H + K + R) | 149 | 10.1 | 13 | 15.9 |
| Acidic | (D + E) | 114 | 7.7 | 3 | 3.7 |

Figure 4A:
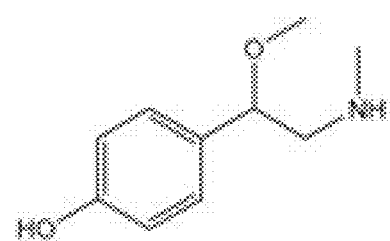
FIGS. 4A to 4D represent SPR analysis of the interaction between purified NUP153 and other charged compounds.
Figure 4B:
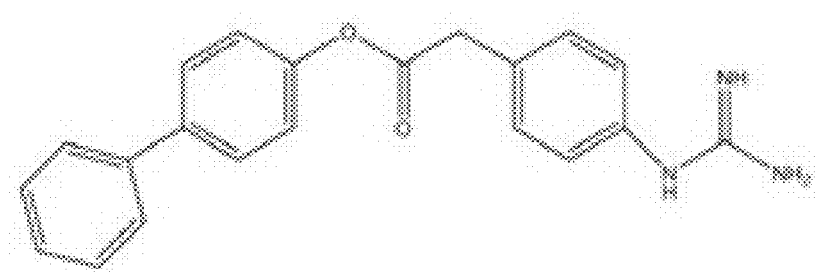
Figure 4C:
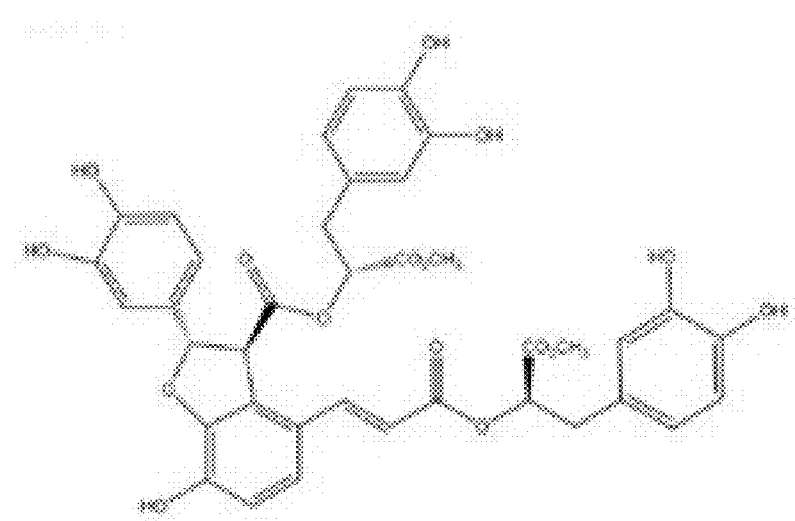
Figure 4D:
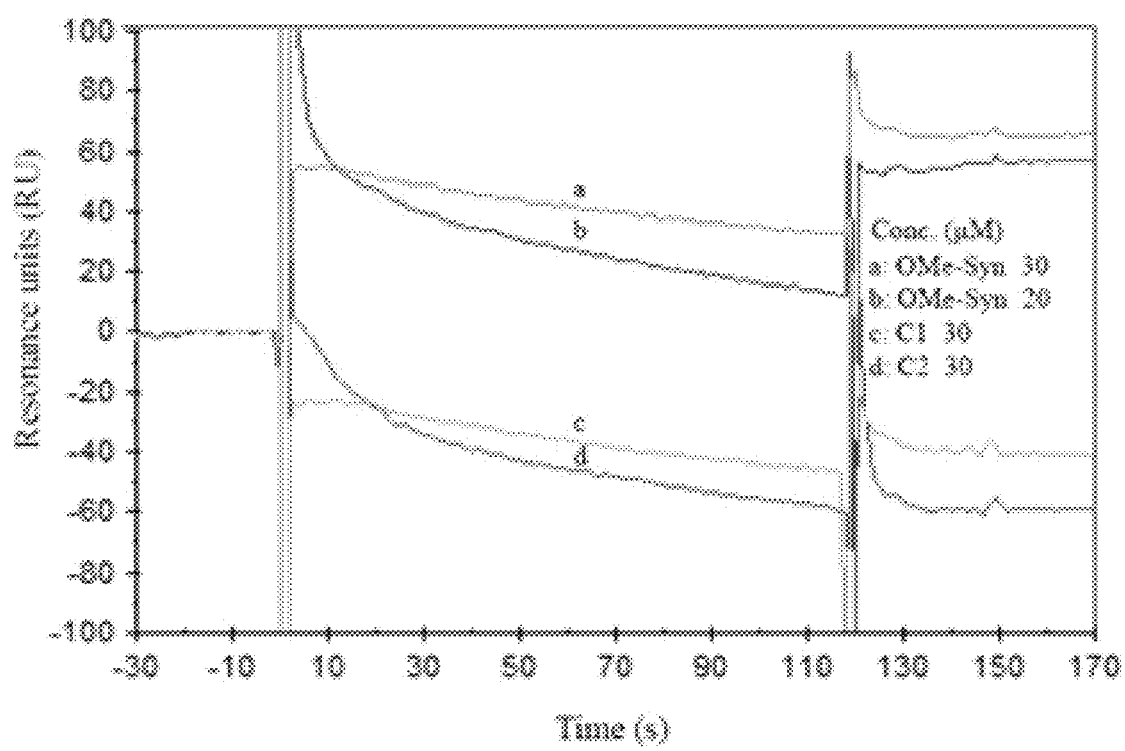

This amino acid composition property change may cause non-specific binding of partial NUP153 to other charged small molecules. To address this possibility, purified NUP153 was applied to OMe-Syn and other charged small molecules, such as biphenyl-4-yl 2-(4-guanidinophenyl)acetate and (2S,3S)—((R)-3-(3,4-dihydroxyphenyl)-1-methoxy-1-oxopropan-2-yl)2-(3,4-dihydroxyphenyl)-4-((E)-3-((R)-3(3,4dihydroxyphenyl)-1-methoxy-1-oxopropan-2-yloxy)-3-oxoprop-1-enyl)-7-hydroxy-2,3-dihydrobenzofuran-3-carboxylate), immobilized on an SPR sensor chip. As a result, NUP153 specifically bound to OMe-Syn and not to other compounds (see FIG. 4D), indicating that the purified domain of NUP153 specifically binds to OMe-Syn.

Figure 3D:
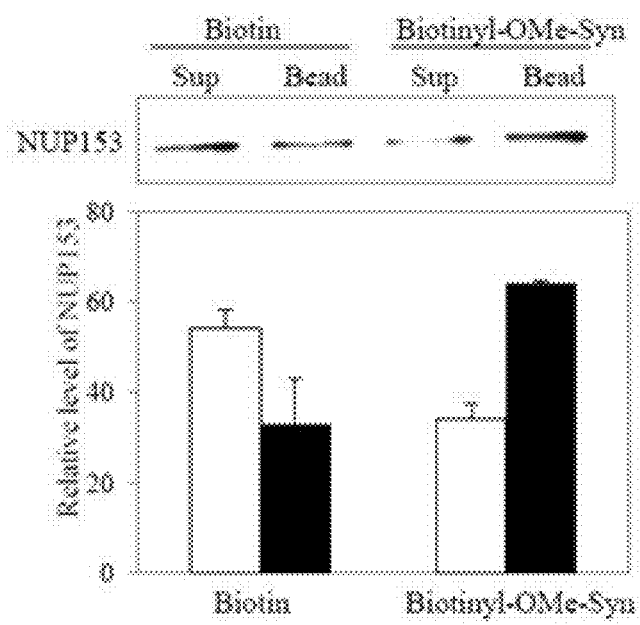

The present inventors further validated OMe-Syn binding to endogenous NUP153 using pull-down assays with HUVEC cell lysate as the proteome source. NUP153 was pulled down from lysates of HUVECs with biotin- and biotinyl-OMe-Syn-conjugated streptavidin agarose beads. Notably, the amount of NUP153 bound to biotinyl-OMe-Syn-conjugated beads (64%) was higher than that of the supernatant (34%), which was validated by western blotting using an antibody against NUP153. In addition, control beads conjugated to biotin without OMe-Syn (32%) did not bind to NUP153 (FIG. 3D). These data indicate that OMe-Syn also binds to intact NUP153. Collectively, NUP153 was identified as a binding protein of OMe-Syn.

Genetic Knockdown of NUP153 Inhibits Angiogenesis

Figure 5A:
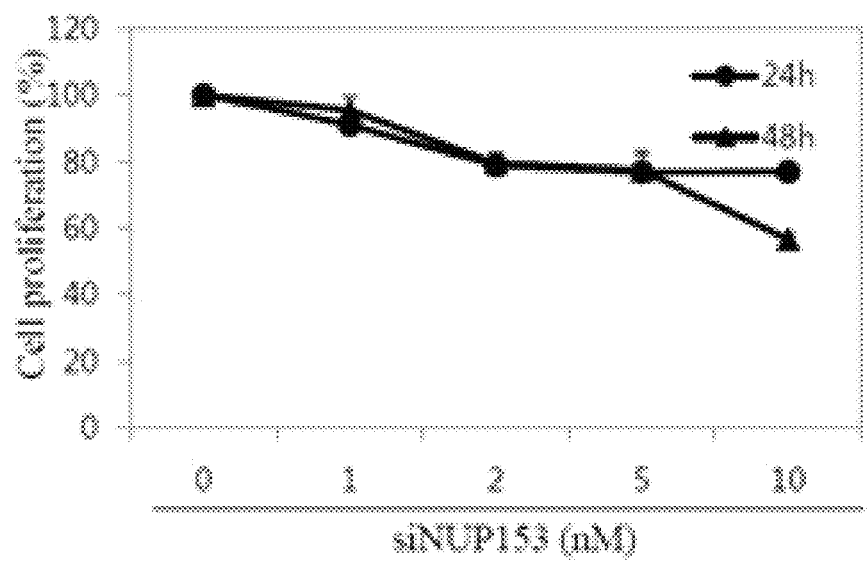
FIGS. 5A to 5D shows role of NUP153 in angiogenesis in vitro.
Figure 5B:
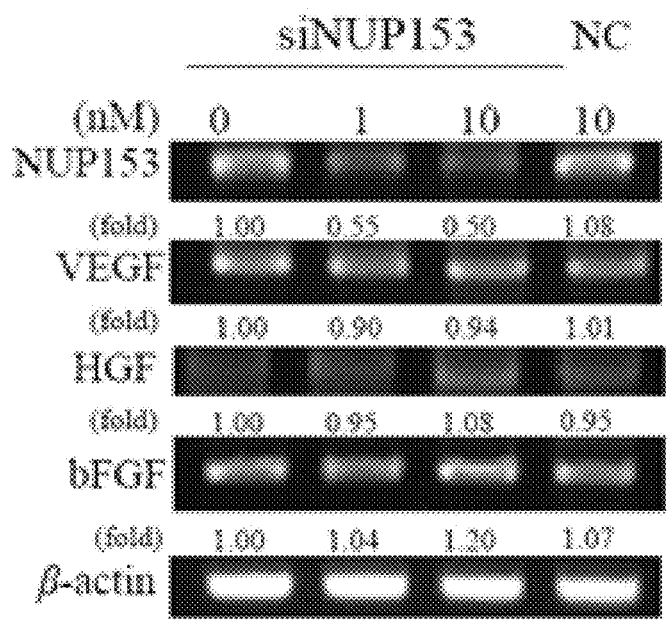
Figure 5C:
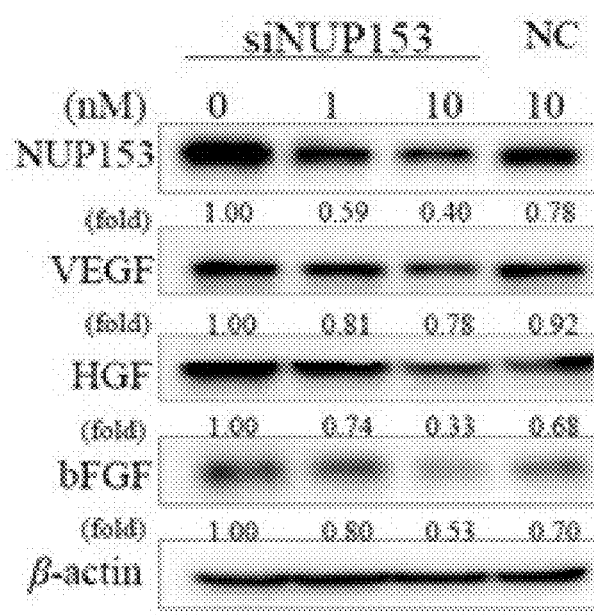
Figure 5D:
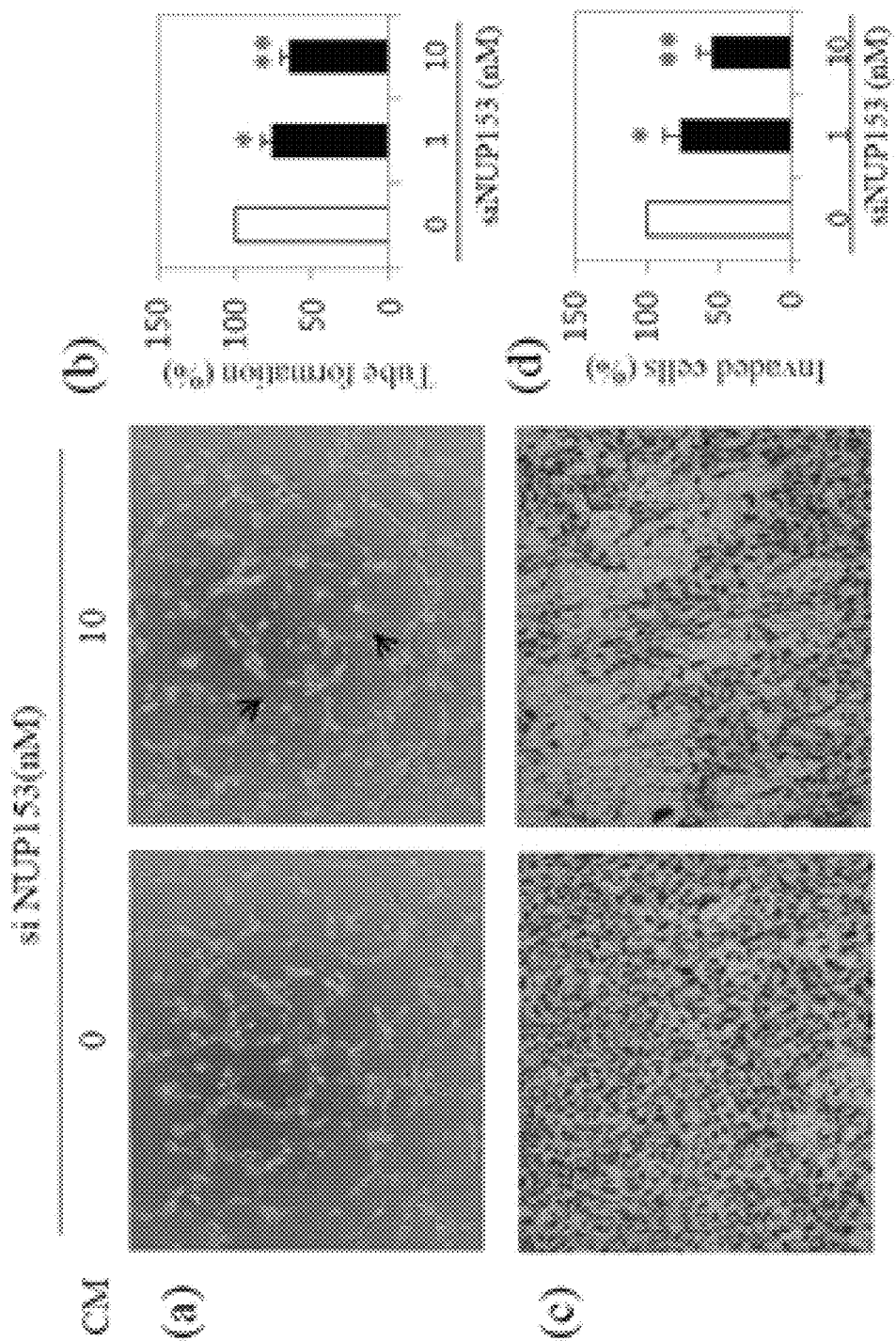

Next, the biological relevancy of OMe-Syn binding to NUP53 for its anti-angiogenesis was investigated by genetic knockdown with NUP153 small interfering RNA (siRNA) in HUVECs. The proliferation of HUVECs was assessed under NUP153-depleted conditions. The efficiency of NUP153 depletion was verified by western blotting (FIG. 5B). The growth of HUVECs with NUP153-knocked down was suppressed in a dose-dependent manner compared with control HUVECs (FIG. 5A). In addition to decreasing cell proliferation, protein expression of pro-angiogenic factors such as VEGF, basic fibroblast growth factor (bFGF) and hepatocyte growth factor (HGF) were also decreased dose dependently by NUP153 depletion (FIG. 5C). This result is concurred with treatment of OMe-Syn as shown in the previous report (Kim et al., 2010). Other housekeeping genes, β-actin, was not largely affected. However, there was no significant change of mRNA level of those proteins (FIG. 5B). These results suggested that knock-down of NUP153 may affect the export of mRNA of pro-angiogenic factors from nucleus leading to suppression of angiogenesis. Furthermore, an in vitro angiogenesis assay was conducted using conditioned medium (CM) of HeLa cells with NUP153-knocked down. Treatment of HUVECs with CM showed less activity in respect with chemo-invasion and tube formation in a dose-dependent manner without showing toxicity (FIG. 5D).

Figure 6A:
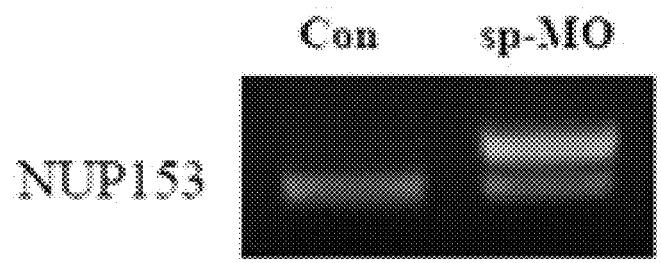
FIGS. 6A through 6E represent that NUP153 is required for ISV angiogenesis in zebrafish embryos.
Figure 6B:
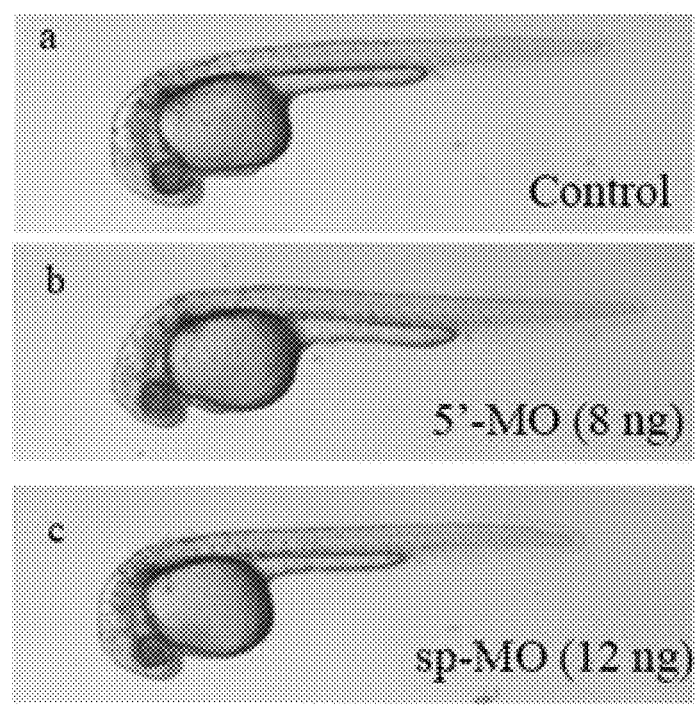
Figure 6C:
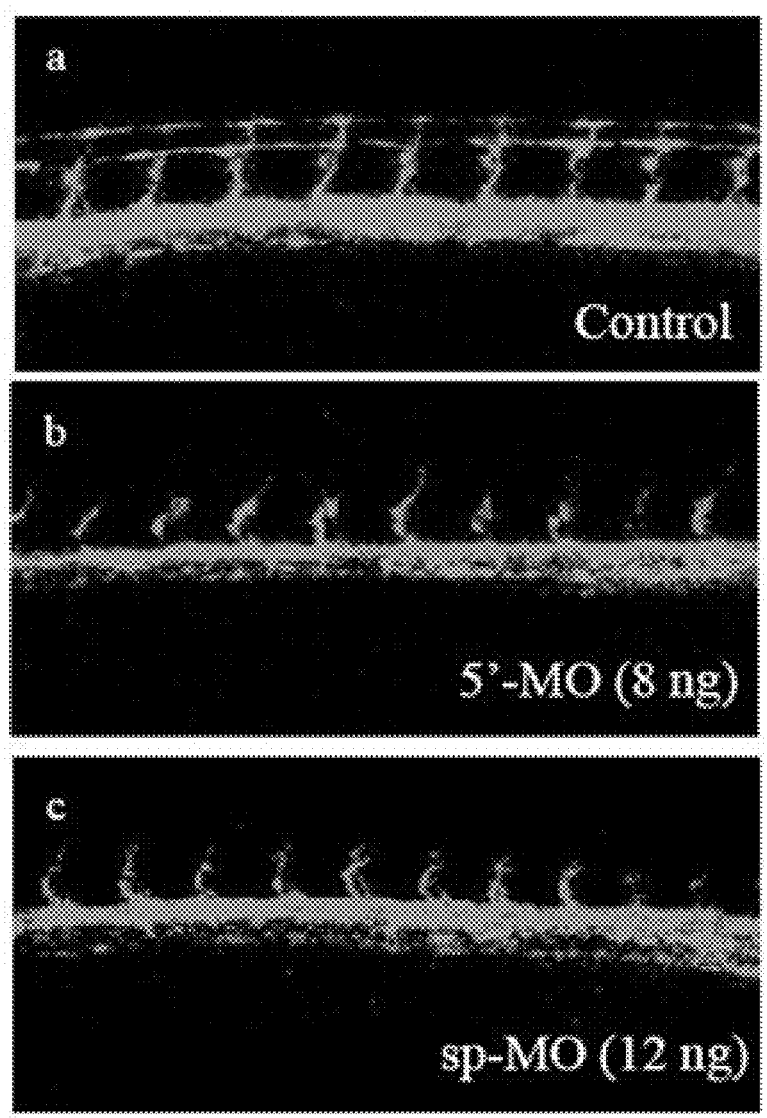
Figure 6D:
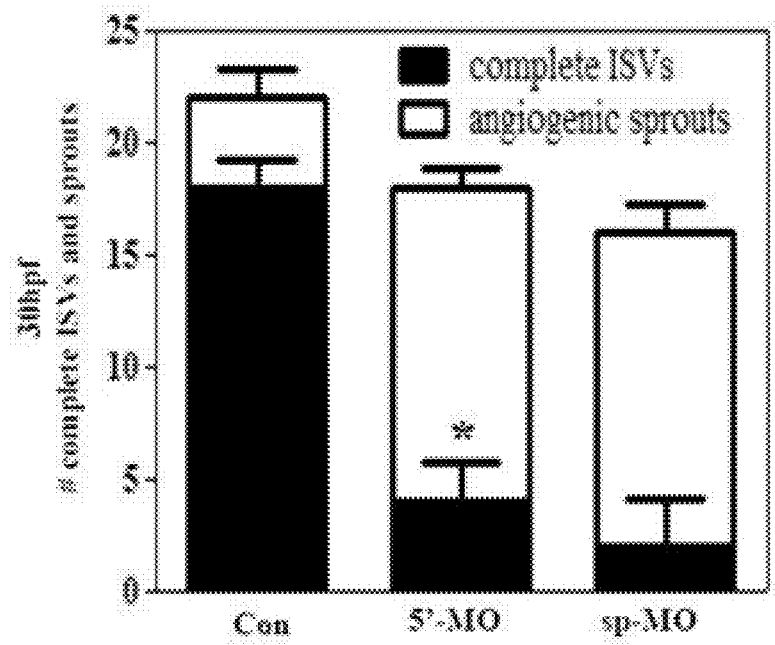
Figure 6E:
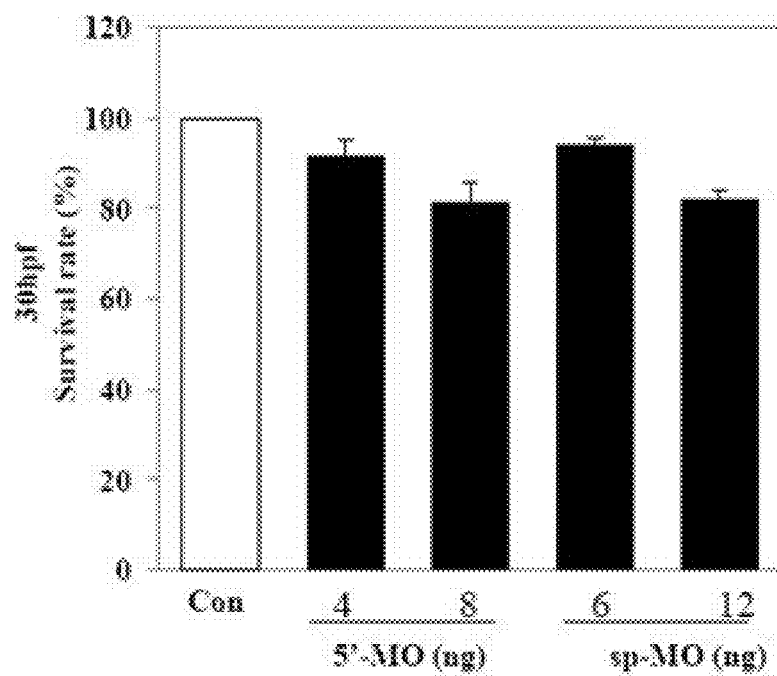

The present inventors further examined the function of NUP153 in vivo in intersegmental vessel (ISV) angiogenesis of zebrafish embryos using a morpholino oligonucleotide (MO) specific to NUP153. NUP153-specific MOs that block the splicing (n=31) or translation (n=28) of NUP153 were injected into fli1a:EGFP transgenic embryos at the one-cell stage. The blocking of NUP153 splicing was monitored by reverse transcription-polymerase chain reaction (RT-PCR) (FIG. 6A). Notably, at 30 hpf, the two types of NUP153-MO-injected embryos showed a decrease in the number and extent of ISV formation compared with control embryos without toxicity (FIG. 6B to 6E). These data demonstrate that NUP153 could be a biologically relevant target of OMe-Syn and play a crucial role in vessel formation and angiogenesis in vitro and in vivo.

Anti-Retina Angiogenesis Activity of OMe-Syn

Figure 7A:
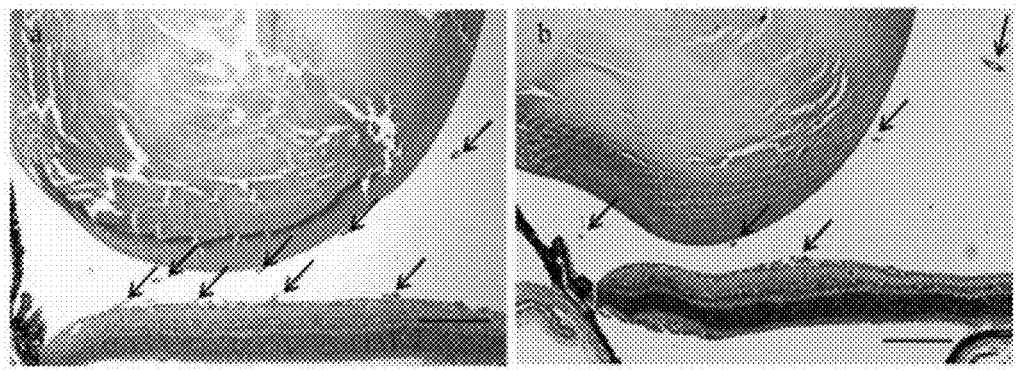
FIGS. 7A to 7C represent effect of OMe-Syn on retinal neovascularization in OIR.
Figure 7B:
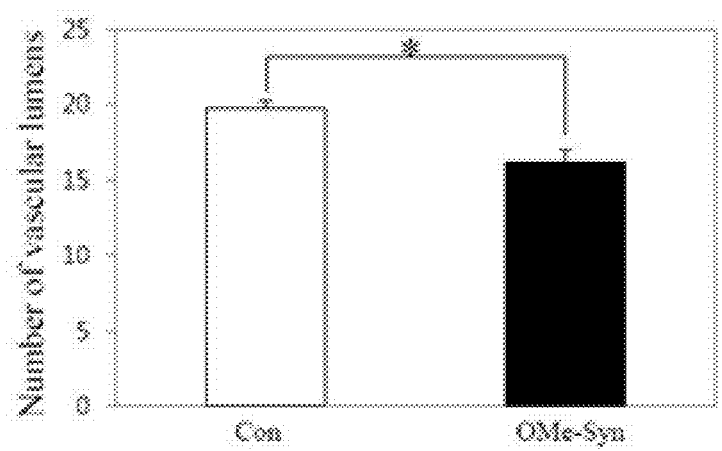
Figure 7C:
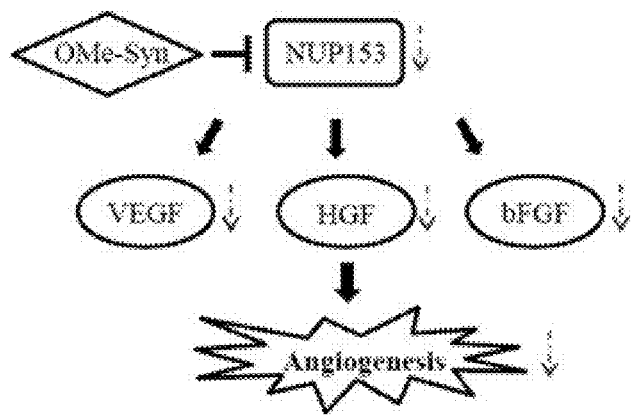

The present inventors investigated whether OMe-Syn could inhibit retinal neovascularization in oxygen-induced retinopathy (OIR). OMe-Syn was intravitreously injected on postnatal day 14 (P14) of OIR and at P17, the inhibitory effect of the compound was examined. To quantitatively evaluate the effect of OMe-Syn on retinal neovascularization, vascular lumens between posterior surface of lens and anterior surface of the inner limiting membrane were counted in a masked fashion. As a result, OMe-Syn treated group effectively reduced number of vascular lumens compared to control group (FIG. 7B), suggesting its new medical treatment for OIR retinopathy.

Discussion

Target identification and validation of bioactive small molecule plays one of key roles in chemical biology. This provides insights into new functional roles of target protein and its gene in biology and better drug development. Applying a unique bioactive small molecule with phage display biopanning based target identification, NUP153, one of components in nuclear pore complex (NPC), was firstly identified as a biologically relevant target protein of anti-angiogenic small molecule, OMe-Syn. Many studies on NUP153 and its interacting cargo proteins, as well as transport receptors, have been reported (Ball et al., 2007; Marg et al., 2004). Yet, no study has reported a small molecule as a binding ligand of NUP153 and role of NUP153 in angiogenesis, either. Accordingly, the role of NUP153 in angiogenesis by using this new small molecule targeting NUP153 including genetic means was investigated in cell and animal models.

A number of binding experiments were conducted to validate and exclude off-target effect between NUP153 and OMe-Syn. First, phage binding and competition assay were carried out using NUP153 and other binding protein-expressing phages of OMe-Syn from DNA sequencing. As a result, OMe-Syn specifically bound to NUP153-expressing phage (FIGS. 3A and 3B). Next, based on the molecular properties of the amino acids of the isolated protein, the effect of differently charged small molecules, such as biphenyl-4-yl 2-(4-guanidinophenyl)acetate and (2S,3S)—((R)-3-(3,4-dihydroxyphenyl)-1-methoxy-1-oxopropan-2-yl)2-(3, 4-dihydroxyphenyl)-4-((E)-3-((R)-3(3,4dihydroxyphenyl)-1-methoxy-1-oxopropan-2-yloxy)-3-oxoprop-1-enyl)-7-hydroxy-2,3-dihydrobenzofuran-3-carboxylate), was assessed through SPR analysis (FIGS. 4A to 4D). The result of this analysis verified that NUP153 specifically bound to OMe-Syn and not other charged small molecules tested in this study. Together, these results demonstrated that OMe-Syn binds to NUP153 with specificity.

NUP153 is one of components of the NPC, and it remains to be determined in respect with the effect of OMe-Syn on NPC formation and transport of proteins or mRNA. Our preliminary investigation suggests that OMe-Syn treatment leaves the NPC intact and does not disrupt NPC protein interactions, suggesting that the NPC is intact even with OMe-Syn treatment. Notably, knock-down of NUP153 by siRNA suppressed the expression of pro-angiogenic factors including VEGF, bFGF and HGF with no significant reduction of mRNA of these factors, indicating that NUP153 involves in nucleus export of these mRNAs (FIGS. 6A to 6E). Other housekeeping genes such as β-actin and GAPDH were not largely affected partially because of abundance of these proteins. Accordingly, binding of OMe-Syn to NUP153 leads to inhibition of mRNA export from nucleus resulted in suppression of expression of angiogenesis related genes. Consequently, OMe-Syn exhibits anti-angiogenic activities in vitro and in vivo. The simple but distinct structure of OMe-Syn from known angiogenesis inhibitors could be a valuable template to generate new OMe-Syn-inspired synthetic compounds for structure-activity relationship studies as well as for developing more specific derivatives with better potency for its target protein, NUP153. Collectively, target identification of the natural small molecule OMe-Syn, based on unbiased affinity-based purification using the human cDNA-expressed proteome of T7 phages sheds light on NUP153 as a new player in angiogenesis. This new information regarding the molecular interaction of small molecule (OMe-Syn) and its partner protein (NUP153) will provide a new basis to explore and control angiogenesis.

Having described a specific embodiment of the present invention, it is to be understood that variants and modifications thereof falling within the spirit of the invention may become apparent to those skilled in this art, and the scope of this invention is to be determined by appended claims and their equivalents.

REFERENCES

Ahn, N. G. (2009). PORE-ing over ERK substrates. *Nat. Struct. Mol. Biol* 16, 1004-1005.

Ball, J. R., Dimaano, C., Bilak, A., Kurchan, E., Zundel, M. T., and Ullman, K. S. (2007). Sequence preference in RNA recognition by the nucleoporin Nup153. *J. Biol. Chem* 282, 8734-8740.

Cheong, H. J., Lee, K. S., Woo, I. S., Won, J. H., and Byun, J. H. (2011). Up-regulation of the DR5 expression by proteasome inhibitor MG132 augments TRAIL-induced apoptosis in soft tissue sarcoma cell lines. *Cancer Res. Treat* 43, 124-130.

Cong, F., Cheung, A. K., and Huang, S. M. (2012). Chemical genetics-based target identification in drug discovery. *Annu. Rev. Pharmacol. Toxicol* 52, 57-78.

Fahrenkrog, B., Maco, B., Fager, A. M., Koser, J., Sauder, U., Ullman, K. S., and Aebi, U. (2002). Domain-specific antibodies reveal multiple-site topology of Nup153 within the nuclear pore complex. *J. Struct. Biol* 140, 254-267.

Firestone, A. J., Weinger, J. S., Maldonado, M., Barlan, K., Langston, L. D., O'Donnell, M., Gelfand, V. I., Kapoor, T. M., and Chen, J. K. (2012). Small-molecule inhibitors of the AAA+ ATPase motor cytoplasmic dynein. *Nature* 484, 125-129.

Furuichi, Y., Maeda, M., Moriguchi, A., Sawamoto, T., Kawamura, A., Matsuoka, N., Mutoh, S., and Yanagihara, T. (2003). Tacrolimus, a potential neuroprotective agent, ameliorates ischemic brain damage and neurologic deficits after focal cerebral ischemia in nonhuman primates. *J. Cereb. Blood. Flow. Metab* 23, 1183-1194.

Giles, F. J., Cooper, M. A., Silverman, L., Karp, J. E., Lancet, J. E., Zangari, M., Shami, P. J., Khan, K. D., Hannah, A. L., Cherrington, J. M., et al. (2003). Phase II study of SU5416—a small-molecule, vascular endothelial growth factor tyrosine-kinase receptor inhibitor—in patients with refractory myeloproliferative diseases. *Cancer* 97, 1920-1928.

Harding, M. W., Galat, A., Uehling, D. E., and Schreiber, S. L. (1989). A receptor for the immunosuppressant FK506 is a cis-trans peptidyl-prolyl isomerase. *Nature* 341, 758-760.

Jung, H. J., Shim, J. S., Lee, J., Song, Y. M., Park, K. C., Choi, S. H., Kim, N. D., Yoon, J. H., Mungai, P. T., Schumacker, P. T., et al. (2010). Terpestacin inhibits tumor angiogenesis by targeting UQCRB of mitochondrial complex III and suppressing hypoxia-induced reactive oxygen species production and cellular oxygen sensing. *J. Biol. Chem* 285, 11584-11595.

Jusko, W. J., Piekoszewski, W., Klintmalm, G. B., Shaefer, M. S., Hebert, M. F., Piergies, A. A., Lee, C. C., Schechter, P., and Mekki, Q. A. (1995). Pharmacokinetics of tacrolimus in liver transplant patients. *Clin. Pharmacol. Ther* 57, 281-290.

Kau, T. R., Way, J. C., and Silver, P. A. (2004). Nuclear transport and cancer: from mechanism to intervention. *Nat. Rev. Cancer* 4, 106-117.

Kim, N. H., Pham, N. B., Quinn, R. J., and Kwon, H. J. (2010). R-(−)-beta-O-methylsynephrine, a natural product, inhibits VEGF-induced angiogenesis in vitro and in vivo. *Biochem. Biophys. Res. Commun* 399, 20-23.

Lin, X., David, C. A., Donnelly, J. B., Michaelides, M., Chandel, N. S., Huang, X., Warrior, U., Weinberg, F., Tormos, K. V., Fesik, S. W., et al. (2008). A chemical genomics screen highlights the essential role of mitochondria in HIF-1 regulation. *Proc. Natl. Acad. Sci. USA* 105, 174-179.

Lindsay, M. A. (2003). Target discovery. *Nat. Rev. Drug. Discov* 2, 831-838.

Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. *Cell* 66, 807-815.

Lomenick, B., Olsen, R. W., and Huang, J. (2011). Identification of direct protein targets of small molecules. *ACS. Chem. Biol* 6, 34-46.

Mackay, D. R., Elgort, S. W., and Ullman, K. S. (2009). The nucleoporin Nup153 has separable roles in both early mitotic progression and the resolution of mitosis. *Mol. Biol. Cell* 20, 1652-1660.

Marg, A., Shan, Y., Meyer, T., Meissner, T., Brandenburg, M., and Vinkemeier, U. (2004). Nucleocytoplasmic shuttling by nucleoporins Nup153 and Nup214 and CRM1-dependent nuclear export control the subcellular distribution of latent Stat1. *J. Cell. Biol* 165, 823-833.

Markman, M. (2008). Refocusing the debate: evidence-based clinical cancer research versus marketplace reality. *J. Oncol. Pract* 4, 231.

Orlic, M., Spencer, C. E., Wang, L., and Gallie, B. L. (2006). Expression analysis of 6p22 genomic gain in retinoblastoma. *Genes Chromosomes Cancer* 45, 72-82.

Piggott, A. M., and Karuso, P. (2008). Rapid identification of a protein binding partner for the marine natural product kahalalide F by using reverse chemical proteomics. *Chem Bio Chem* 9, 524-530.

Sato, S., Murata, A., Orihara, T., Shirakawa, T., Suenaga, K., Kigoshi, H., and Uesugi, M. (2011). Marine natural product aurilide activates the OPA1-mediated apoptosis by binding to prohibitin. *Chem. Bio* 118, 131-139.

Shim, J. S., Lee, J., Park, H. J., Park, S. J., and Kwon, H. J. (2004). A new curcumin derivative, HBC, interferes with the cell cycle progression of colon cancer cells via antagonization of the Ca2+/calmodulin function. *Chem. Biol* 11, 1455-1463.

Siekierka, J. J., Hung, S. H., Poe, M., Lin, C. S., and Sigal, N. H. (1989). A cytosolic binding protein for the immunosuppressant FK506 has peptidyl-prolyl isomerase activity but is distinct from cyclophilin. *Nature* 341, 755-757.

Smith, L. E., Wesolowski, E., McLellan, A., Kostyk, S. K., D'Amato, R., Sullivan, R., and D'Amore, P. A. (1994). Oxygen-induced retinopathy in the mouse. *Invest. Ophthalmol. Vis. Sci* 35, 101-111.

Vasu, S. K., and Forbes, D. J. (2001). Nuclear pores and nuclear assembly. *Curr. Opin. Cell Biol* 13, 363-375.

Walther, T. C., Fornerod, M., Pickersgill, H., Goldberg, M., Allen, T. D., and Mattaj, I. W. (2001). The nucleoporin Nup153 is required for nuclear pore basket formation, nuclear pore complex anchoring and import of a subset of nuclear proteins. *EMBO J* 20, 5703-5714.

Westerfield, M. (1995). The zebrafish book: a guide for the laboratory use of zebrafish (*Danio rerio*), Ed. 3. ed (Eugene, Oreg.: M. Westerfield).

Zhang, D., Kaufman, P. L., Gao, G., Saunders, R. A., and Ma, J. X. (2001). Intravitreal injection of plasminogen kringle 5, an endogenous angiogenic inhibitor, arrests retinal neovascularization in rats. *Diabetologia* 44, 757-765.

What is claimed is:
1. A method for treating a disease selected from the group consisting of cancer, diabetic retinopathy, retinopathy of prematurity, neovascular glaucoma, and proliferative retinopathy, the method comprising:
administering to a subject in need thereof a biotinylated OMe-Syn of Compound 1:
[Compound 1]
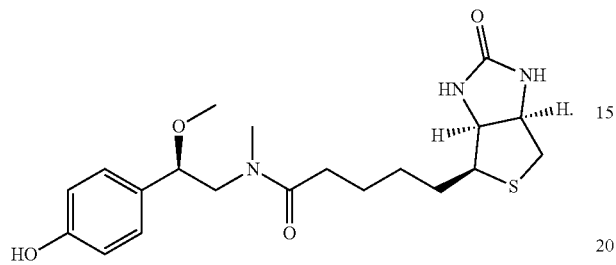
* * * * *